United States Patent
Northey et al.

(10) Patent No.: US 10,617,715 B2
(45) Date of Patent: Apr. 14, 2020

(54) METHODS OF TREATING OR PREVENTING BIOFILM ASSOCIATED INFECTIONS WITH FREE AVAILABLE CHLORINE FREE AVAILABLE CHLORINE WATER

(75) Inventors: Robert Northey, Petaluma, CA (US); Eileen Thatcher, Petaluma, CA (US); Andres Gutierrez, Petaluma, CA (US)

(73) Assignee: Sonoma Pharmaceuticals, Inc., Petaluma, CA (US)

( * ) Notice: Subject to any disclaimer, the term of this patent is extended or adjusted under 35 U.S.C. 154(b) by 0 days.

(21) Appl. No.: 12/645,419

(22) Filed: Dec. 22, 2009

(65) Prior Publication Data

US 2010/0166809 A1    Jul. 1, 2010

Related U.S. Application Data

(60) Provisional application No. 61/139,972, filed on Dec. 22, 2008.

(51) Int. Cl.
*A61K 33/20* (2006.01)

(52) U.S. Cl.
CPC .................................. *A61K 33/20* (2013.01)

(58) Field of Classification Search
USPC ........................................................ 424/400
See application file for complete search history.

(56) References Cited

U.S. PATENT DOCUMENTS

| | | | |
|---|---|---|---|
| 5,919,129 A * | 7/1999 | Vandre ...................... | A61B 1/07 433/29 |
| 6,762,160 B2 * | 7/2004 | Barbeau et al. ............... | 510/161 |
| 2004/0062818 A1 | 4/2004 | Calderon | |
| 2005/0139808 A1 | 6/2005 | Alimi | |
| 2006/0253060 A1 * | 11/2006 | Alimi .............................. | 604/19 |

FOREIGN PATENT DOCUMENTS

| WO | WO 2005/065383 A2 | 7/2005 |
|---|---|---|
| WO | WO 2005/117914 A2 | 12/2005 |
| WO | WO 2007/085018 A2 | 7/2007 |
| WO | WO 2008/089268 A2 | 7/2008 |
| WO | WO 2008/112940 A1 | 9/2008 |

OTHER PUBLICATIONS

Hoffmann et al. (Antimicrobial Agents and Chemotherapy, Oct. 2007, p. 3677-3687).*
Ymele-Leki et al. (Applied and Environmental Microbiology, Mar. 2007, p. 1834-1841).*
Tanaka et al. (Clin Rheumatol (2005) 25: 65-69).*
Morris and Hagr (The Journal of Otolaryngology, vol. 34, Supplement 2, Aug. 2005, pp. S56-S59).*
Plontke et al. (Adv Otorhinolaryngol. 2002;59:149-55).*
Delloyd (delloyd.50megs.com/ppm.html).*
Hybrid (Hybrid info sheet).*
Thurnheer (Applied and Environmental Microbiology, Mar. 2003, p. 1702-1709).*
Holmes (Journal of Industrial Microbiology (1995) 15, 208-213).*
Perezous (J Prosthet Dent. Mar. 2005;93(3):288-93).*
Soucek (Progress in Human Auditory and Vestibular Histopathology, Kugler Publications, Jan. 1, 1997, pp. 117-123).*
DeBeer et al., Appl. Environ. Microbiol. 60:4339-44 (1994).*
Anderson (Science vol. 301 Jul. 4, 2003, pp. 105-107).*
Badalament (Cancer 601423-1427,1987).*
Carson (Journal of Urology, vol. 161, pp. 338-341; Jan. 1999).*
Sena (International Endodontic Journal, 39, 878-885, 2006).*
Zambon (Journal of Periodontology Nov. 1990, vol. 61, No. 11, pp. 699-704).*
Sixou (Oral Oncol Eur J Cancer vol. 32B, No. 5, pp. 306-310, 1996).*
International Search Report issued in PCT Application No. PCT/US09/69345, dated Jun. 25, 2010.
Rutala et al., *Infect. Control Hosp. Epidemiol.*, "Stability and Bactericidal Activity of Chlorine Solutions," 19(5):323-327 (1998).

* cited by examiner

*Primary Examiner* — Devang K Thakor
(74) *Attorney, Agent, or Firm* — Leydig, Voit & Mayer, Ltd.

(57) ABSTRACT

The invention provides methods of treating or reducing the incidence of an infection in a mammal due to a biofilm associated infectious microorganism comprising administering a therapeutically effective amount of free available chlorine (FAC) water to a site populated with biofilm associated infectious microorganism.

18 Claims, 9 Drawing Sheets

Upper - OIS 200
Lower - OIS 125

METHODS OF TREATING OR PREVENTING BIOFILM ASSOCIATED INFECTIONS WITH FREE AVAILABLE CHLORINE FREE AVAILABLE CHLORINE WATER

CROSS-REFERENCE TO RELATED APPLICATIONS

This patent application claims the benefit of U.S. Provisional Patent Application No. 61/139,972, filed Dec. 22, 2008; which is hereby incorporated by reference in its entirety.

BACKGROUND OF THE INVENTION

Biofilms are surface attached microbial communities that can be found at almost any solid-liquid interface in industrial, environmental and clinical settings. There is compelling evidence that the biofilm lifestyle is an efficient means for microorganisms to define and maintain a protected niche. Biofilm associated infections cause significant morbidity and mortality. For example, the opportunistic bacterial pathogen *Pseudomonas aeruginosa* is responsible for persistent infections associated with cystic fibrosis (CF) lung disease, burn wounds, otorrhea, and the cornea. One of the major factors contributing to the recalcitrant nature of these infections is the ability of *P. aeruginosa* to form biofilms in these tissues.

Biofilm associated infections can also be caused by, e.g., several species of *Streptococcus, Staphylococcus aureus, Haemophilus influenzae, Burkholderia cepacia, E. coli,* and several species of *Candida*. Other specific infections diseases associated with biofilms include, e.g., native valve endocarditis, otitis media, chronic bacterial prostatitis, and periodontitis.

Bacteria growing in biofilms can become up to 1000-fold more resistant to antibiotics and other biocides as compared to their non-biofilm associated (or "planktonic") counterparts. As a result of this increased resistance, biofilm infections cannot be effectively treated with conventional antibiotic therapy. There is not a single mechanism that can be ascribed to the tenacious biofilm phenotype, which is believed to arise from a multiplicity of factors, including poor antimicrobial penetration, oxygen and nutrient limitation, slow growth, and adaptive stress responses.

Similarly, a number of medical devices have been shown to be susceptible to colonization by bacteria in biofilms. For certain devices, such as urinary catheters and contact lenses, research has also elucidated the susceptibility of various materials to bacterial adhesion and biofilm formation. Urinary catheter biofilms are unique in that certain of the component organisms may alter the local pH through the production of urease, which hydrolyzes the urea of the urine to form free ammonia which, in turn, will raise the local pH and allow precipitation of minerals such as calcium phosphate (hydroxyapatite) and magnesium ammonium phosphate (struvite). These minerals will then deposit in the catheter biofilms, forming a mineral encrustation. The primary urease-producing organisms in urinary catheters are *P. mirabilis, M. morganii, P. aeruginosa, K. pneumoniae,* and *Proteus vulgaris*. Organisms that have been shown to adhere to contact lenses include *P. aeruginosa, S. aureus, S. epidermidis, Serratia* spp., *E. coli, Proteus* spp., and *Candida* spp. In addition, biofilms on specific devices, such as, e.g., prosthetic heart valves, central venous catheters, urinary (Foley) catheters, contact lenses, intrauterine devices, and dental unit water lines present significant clinical challenges.

Thus, the findings clearly indicate the need for new antimicrobial agents and biocides and methods of their use that are effective against biofilms. The present invention provides such methods. These and other advantages of the invention, as well as additional inventive features, will be apparent from the description of the invention provided herein.

BRIEF SUMMARY OF THE INVENTION

The invention provides methods of treating or reducing the incidence of an infection in a mammal comprising administering a therapeutically effective amount of free available chlorine (FAC) water to a biofilm containing an infectious microorganism present on the surface of a tissue wherein: (a) the pH of the FAC water is from about 4.5 to about 7.7, (b) the concentration of oxychlorine species in the FAC water is at least about 30 mg/L, and (c) the tissue on which the biofilm is present is selected from the group consisting of lower and upper respiratory tract tissue, corneal tissue, inner ear tissue, urinary tract tissue, oral mucosa tissue, dental tissue and synovial tissue. The invention further provides methods for treating or reducing the incidence of an infectious microorganism is in a preinfectious commensal state.

The invention also provides methods reducing the incidence of an infection in a mammal associated with a medical device comprising contacting the medical device with an effective amount of free available chlorine (FAC) water to wherein: (a) the pH of the FAC water is from about 4.5 to about 7.7, (b) the concentration of oxychlorine species in the FAC water is at least about 30 mg/L, and (c) a biofilm containing an infectious microorganism is present on the surface of the device.

The invention further provides methods for treating, reducing or preventing the incidence of a bacterial infection in a mammal comprising administering a therapeutically effective amount of FAC water to the site of an infection present on the surface of a tissue wherein the FAC water can reduce the concentration of bacteria in biofilms by at least about four logs ($10^4$) within about sixty minutes (60) of continuous exposure of the bacteria in biofilms to the FAC water.

Infectious microorganisms which can be treated, reduced or otherwise controlled by methods in accordance with the invention include, e.g., without limitation, yeast, mycobacteria, bacteria or combination thereof. Suitable mammals for the applications of methods in accordance with the invention, include, e.g., human patients. Conditions susceptible methods in accordance with the invention, include, e.g., dental plaque, acute and chronic sinusitis, laryngitis, chronic obstructive pulmonary disease, cystic fibrosis, asthma, extrinsic allergic alveolitis (also known as hypersensitivity pneumonitis), pneumonia, pulmonary tuberculosis, pulmonary fibrosis, pneumocele, pleuritis, ventilator pneumonitis and combinations thereof.

The invention, in yet other embodiments, also provides methods for reducing or preventing symptoms associated with allergic inflammatory reactions in the upper and lower respiratory tract of a mammal comprising administering a therapeutically effective amount of FAC water to a site containing inflammatory cells, wherein the secretion of TNF-alpha and MIP1-alpha by the inflammatory cells is inhibited by at least about 50% and at least about 25% respectively.

Methods in accordance with the invention for administering FAC water include, e.g., administering FAC water using an endoscope and wherein the FAC water is administered as, e.g., a lavage, drop, rinse, spray, mist, aerosol, steam or combination thereof. Accordingly, the FAC water can be administered in accordance with the invention, e.g., in the form of droplets having a diameter in the range of from about 0.1 micron to about 100 microns.

DETAILED DESCRIPTION OF THE INVENTION

Figure 1:
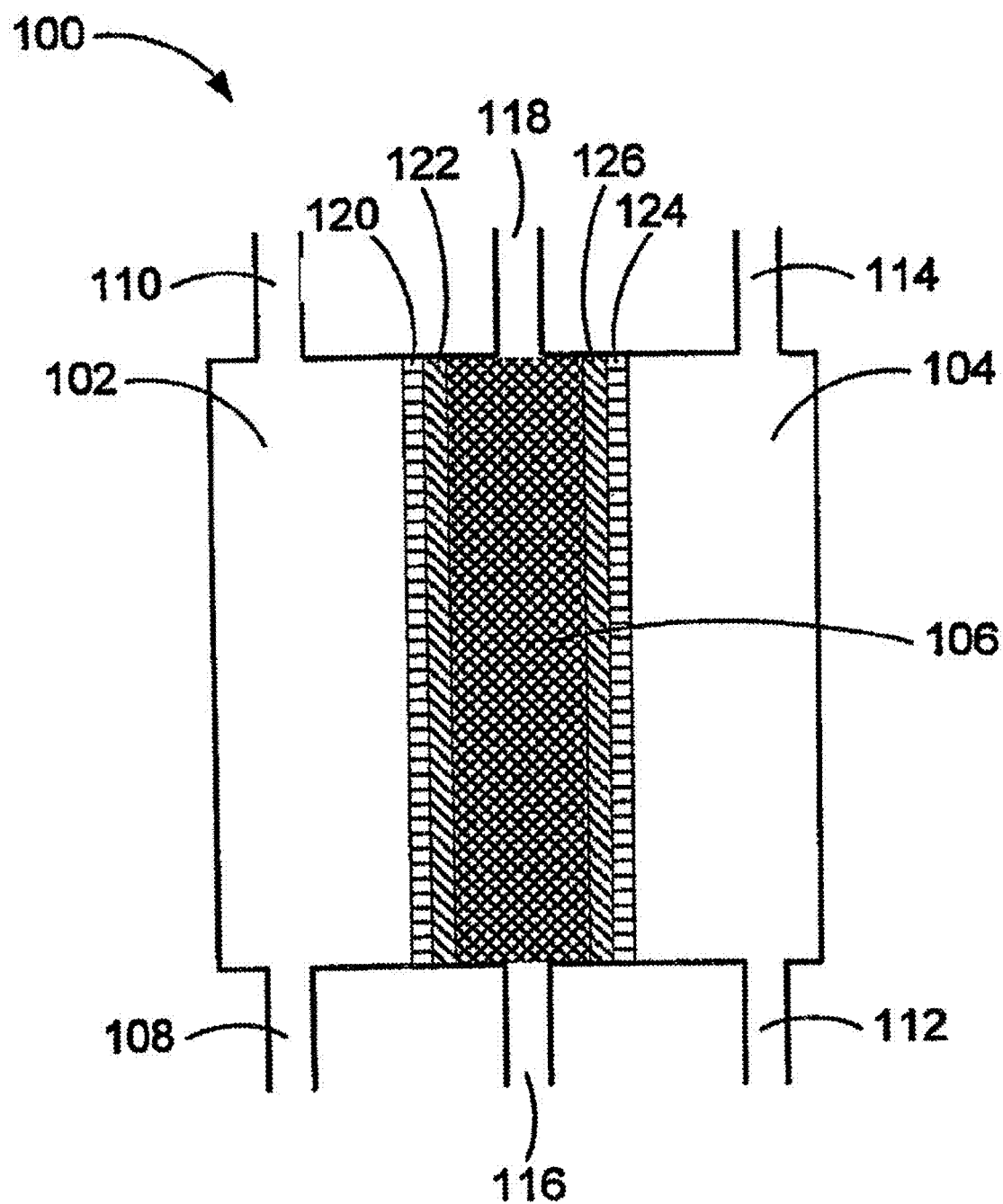
FIG. 1 illustrates a three-chambered electrolysis cell for producing an exemplary FAC water.

The present invention provides a method of preventing or treating biofilm associated infections in a patient, which method comprises administering to the patient a therapeutically effective amount of free available chlorine (FAC) water, wherein the FAC water is stable for at least about twenty-four hours. The method of the present invention can be used for treating or preventing (e.g., inhibiting the onset of, inhibiting the escalation of, decreasing the likelihood of) acute and chronic biofilm associated infections.

The term "treating," as used herein means affecting a cure, reducing the infectious micro-organism population and/or ameliorating the signs and symptoms of a condition or disease.

By "reducing the incidence of an infection in a mammal," as used herein it is meant decreasing the incidence of infection by at least about 5%, preferably by at least about 10%, more preferably by at least about 20%, even more preferably by at least about 25%, even more preferably by at least about 50%, even more preferably by at least about 2-fold, even more preferably by at least about 5-fold, even more preferably by at least about 10-fold, even more preferably by at least about 100-fold even more preferably by at least about 100-fold, and most preferably by at least about 1.000-fold.

The term "a therapeutically effective amount," as used herein, refers to an amount that is adequate (sufficient) to treat a disease or condition such as, e.g., an infection or colonization.

By "contacting the medical device with an effective amount," as used herein, it is meant bringing an adequate (sufficient) amount into a close enough physical proximity to effect the goals of the claim.

As used herein, the term "mg/L" is essentially the same as "ppm" (on a weight basis) since the density of the FAC water of the present invention is 1.0 g/mL.

The invention provides methods of treating or reducing the incidence of an infection in a mammal comprising administering a therapeutically effective amount of free available chlorine (FAC) water to a biofilm containing an infectious microorganism present on the surface of a tissue wherein: (a) the pH of the FAC water is from about 4.5 to about 7.7; (b) the concentration of oxychlorine species in the FAC water is at least about 30 mg/L, typically at least about 80 mg/L, preferably at least about 100 mg/L, more preferably at least about 110 mg/L, most preferably at least about 125 mg/L; and (c) the tissue on which the biofilm is present is selected from the group consisting of lower and upper respiratory tract tissue, corneal tissue, inner ear tissue, urinary tract tissue, oral mucosa tissue, dental tissue and synovial tissue.

In one embodiment of the inventive methods of treating or reducing the incidence of an infection in a mammal, the pH of the FAC water is preferably from about 4.5 to about 6.0. In another embodiment, the pH is preferably from about 6.8 to about 7.6, more preferably from about 7.0 to about 7.5, most preferably from about 7.3 to about 7.5. The invention further provides methods for treating or reducing the incidence of an infectious microorganism is in a preinfectious commensal state.

The invention also provides methods for reducing the incidence of an infection in a mammal associated with a medical device comprising contacting the medical device with an effective amount of free available chlorine (FAC) water to wherein: (a) the pH of the FAC water is from about 4.5 to about 7.7; (b) the concentration of oxychlorine species in the FAC water is at least about 30 mg/L, typically at least about 80 mg/L, preferably at least about 100 mg/L, more preferably at least about 110 mg/L, most preferably at least about 125 mg/L; and (c) a biofilm containing an infectious microorganism present on the surface of the device.

In one embodiment of the inventive methods for reducing the incidence of an infection in a mammal associated with a medical device, the pH of the FAC water is preferably from about 4.5 to about 6.0. In another embodiment, the pH is preferably from about 6.8 to about 7.6, more preferably from about 7.0 to about 7.5, most preferably from about 7.3 to about 7.5.

The invention further provides methods for treating, reducing or preventing the incidence of a bacterial infection in a mammal comprising administering a therapeutically effective amount of FAC water to the site of an infection present on the surface of a tissue wherein the FAC water can reduce the concentration of bacteria in biofilms by at least about three logs ($10^3$), preferably at least about four logs ($10^4$), more preferably at least about five logs ($10^5$) within an about thirty minutes (30), preferably an about sixty minutes (60), more preferably an about ninety minutes (90) of continuous exposure of the bacteria in biofilms to the FAC water.

Further, the invention provides methods for treating, reducing or preventing the incidence of a bacterial infection in a mammal, wherein the concentration of bacteria in biofilms is reduced by at least about two to seven logs ($10^2$-$10^7$) within at least about 30 minutes, preferably within at least about 15 minutes, more preferably within at least about 20 minutes of continuous exposure of the bacteria in biofilms to the FAC water. In yet another embodiments, the invention provides methods for treating, reducing or preventing the incidence of a bacterial infection in a mammal, wherein the concentration of bacteria in biofilms in an animal model is reduced by at least about one half log, preferably at least about one log within at least about three minutes, preferably within at least about two minutes of continuous exposure of the bacteria in biofilms to the FAC water or wherein the concentration of biofilm containing an infectious microorganism present on the surface of the device is reduced by at least about five logs ($10^5$), preferably by at least about five and one half logs ($10^{5.5}$), more preferably reduced by at least about six logs ($10^6$), within thirty (30) seconds.

Suitable the infectious microorganisms which can be treated, reduced or otherwise controlled by methods in accordance with the invention include, for example, without limitation, yeast, mycobacteria, bacteria or combination thereof. Suitable mammals for the applications of methods in accordance with the invention, include, e.g., human patients. Conditions susceptible to methods in accordance with the invention, include, e.g., dental plaque, acute and chronic sinusitis, laryngitis, chronic obstructive pulmonary disease, cystic fibrosis, asthma, extrinsic allergic alveolitis (also known as hypersensitivity pneumonitis), pneumonia, pulmonary tuberculosis, pulmonary fibrosis, pneumocele, pleuritis, ventilator pneumonitis and combinations thereof.

The mammal can be, e.g., a human patient with or without an immunodeficiency. Alternatively, the patient treated in accordance with the invention can have, e.g., a condition from the group consisting of cystic fibrosis, corneal infections, chronic obstructive pulmonary disease, and ventilator pneumonitis.

Suitable microorganisms for treatment in accordance with invention include, e.g., infectious microorganism which have a preinfectious commensal state. In addition, suitable microorganisms for treatment in accordance with invention include, e.g., yeast, mycobacteria, bacteria or combination thereof. Particularly suitable microorganism for treatment in accordance with the invention include, e.g., *Pseudomonas* sp., *Haemophilus* sp., *Pneumococcus* sp., *Candida* sp., *Mycobacterium* sp., *Staphylococcus* sp., *Stenotrophomonas* sp., *Streptococcus* sp., *Escherichia* sp., *Mycoplasma* sp., and combinations thereof. Accordingly, the FAC water treatment in accordance with the invention can further comprise administering at least one (or more) therapeutic agent selected from the group consisting of antibiotics, anti-viral agents, and anti-inflammatory agents, and combinations thereof. The methods in accordance with the invention, in particular the FAC water, can reduced the concentration of viable bacteria in the biofilm by at least about 2 logs, preferably about 2.5 logs, and most preferably about 3 logs within a treatment or contact time of about 60 minutes, preferably about 30 minutes, more preferably about 25 minutes, and most preferably about 20 minutes.

The FAC water can be administered in accordance with the invention, e.g., by a endoscope; as a lavage, drop, rinse, spray, mist, aerosol, steam or combination thereof or in the form of droplets having a diameter in the range of from about 0.1 micron to about 100 microns.

The invention, in yet other embodiments, also provides methods for reducing or preventing symptoms associated with allergic inflammatory reactions in the upper and lower respiratory tract of a mammal comprising administering a therapeutically effective amount of FAC water to a site containing inflammatory cells, wherein the secretion of TNF-alpha and MIP1-alpha by the inflammatory cells is inhibited by at least about 50% and at least about 25% respectively.

The invention further provides method of preventing or treating inflammation that results from biofilm associated infections. Surprisingly, it has been found that the FAC water administered in accordance with the invention is a highly effective inhibitor of mast cell degranulation, one of the primary inflammation and allergy-causing biological cascades. The FAC water administered in accordance with the invention inhibits degranulation of mast cells regardless of whether they are activated with an antigen or a calcium ionophore. Also surprisingly, it has been found that the FAC water administered in accordance with the present invention non-selectively inhibits the secretion of pro-inflammatory cytokines in mast cells. For example, the FAC water of the present invention can inhibit the secretion of, e.g., TNF-α and MIP1-α in mast cells. It is believed that the FAC water administered in accordance with the invention also can inhibit the secretion of pro-inflammatory cytokines in other cytokine-secreting cells including, but not limited to, macrophages, monocytes, lymphocytes, macrophages, PMN, fibroblasts and endothelial cells. These findings demonstrate that the FAC water administered in accordance with the present invention should exhibit broad anti-inflammatory efficacy.

The FAC water administered in accordance with the invention preferably inhibits mast cell degranulation by more than about 50% relative to untreated mast cells, more preferably by more than about 80% relative to untreated mast cells, still more preferably by more than about 90% relative to untreated mast cells, and even more preferably by more than about 95% relative to untreated mast cells, when contacted with the FAC water for up to about 30 minutes, more preferably up to about 15 minutes, and still more preferably up to about 5 minutes.

The FAC water administered in accordance with the invention also preferably inhibits the secretion of TNF-α by more than about 50%, more preferably by more than about 60%, still more preferably by more than about 70%, and even more preferably by more than about 85%. Similarly, the FAC water administered in accordance with the invention also preferably inhibits the secretion of MIP1-α by more than 25%, more preferably by more than about 50%, and still more preferably by more than about 60%. In accordance with the method of the invention, secretion of these and that of other cytokines, can be therapeutically inhibited down to certain % by the administration of the FAC water alone or in combination with a diluent (e.g., water), by increasing the concentration of the components of the FAC water, by utilizing special delivery systems and/or by increasing the exposure time. For instance, cytokine secretion can be therapeutically inhibited by administering compositions in which the FAC water is diluted, e.g., by a ratio of up to about 50% (vol./vol.) FAC water/diluent, by a ratio of up to about 25% (vol./vol.) FAC water/diluent, by a ratio of up to about 10% (vol./vol.) FAC water/diluent, by a ratio of up to about 5% (vol./vol.) FAC water/diluent, or even by a ratio of up to about 1% (vol./vol.) FAC water/diluent.

The method of the present invention also can be used for treating or preventing inflammation associated with hypersensitivity resulting from biofilms or their constitutes (e.g., bacteria, fungi, matrix molecules). Historically, hypersensitivity reactions have been classified as one of four types, from which significant disease can result. The FAC water administered in accordance with the invention can be used to treat and/or prevent (e.g., inhibit the onset of, inhibit the escalation of or decrease the likelihood of) one or more of such reactions. Type I hypersensitivity typically results from the combination of an antigen with an antibody bound to a mast cell or basophil. Type I reactions occur within minutes of exposure to the antigen in individuals who have been previously sensitized to the antigen. In humans, Type I reactions are mediated by IgE which has high affinity Fc receptors on mast cells and basophils.

Mast cells' role in Type I hypersensitivity is especially important because they reside in tissues under the epithelial surface near blood vessels and nerves. Multiple clinical symptoms observed in atopic dermatitis, allergic rhinitis and atopic asthma are produced by IgE-antigen stimulation of mast cells located in distinct affected tissues. The currently accepted view of the pathogenesis of atopic asthma is that allergens initiate the process by triggering IgE-bearing pulmonary mast cells (MCs) to release mediators such as histamine, leukotrienes, prostaglandins, kininis, platelet activating factor (PAF), etc. in the so-called early phase of the reaction. In turn, these mediators induce bronchoconstriction and enhance vascular permeability and mucus production. According to this model, following mast cell activation in the late phase, those cells secrete various cytokines, including tumor necrosis factor alpha (TNF-$\alpha$), IL-4, IL-5 and IL-6, which participate in the local recruitment and activation of other inflammatory cells such as eosinophils, basophils, T lymphocytes, platelets and mononuclear phagocytes. These recruited cells, in turn, contribute to the development of an inflammatory response that may then become autonomous and aggravate the asthmatic symptoms. This late phase response constitutes a long term inflammatory process which will induce changes in surrounding tissues. Clinically, Type I reactions can have local effects such as allergic rhinitis, or systemic effects as is found in anaphylaxis which manifests with itching, hives, respiratory distress, and circulatory collapse.

Type II hypersensitivity is mediated by antibodies directed to antigens on the surfaces of cells and in the extracellular space. These antibodies can direct cell lysis or result in opsonization of the target molecules (preparation for phagocytosis by other cells). Alternatively, the antibodies can be directed to and activate cell surface receptors. Conditions resulting from Type II reactions include transfusion reactions, Graves disease (thyrotoxicosis), drug reactions, pernicious anemia, and acute rheumatic fever. In rheumatic fever the antibodies are formed against Streptococcal antigens but, cross-react with human tissues such as heart valves.

Type III hypersensitivity is caused by immune complexes, which are combinations of antibodies and other host immune system proteins, most typically complement proteins. It is the normal function of antibodies to bind and active complement. However, when the resulting macromolecular immune complexes are not adequately processed, they can lead to persistent tissue damage. Macrophages and PMNLs can be activated by immune complexes and lead to the release of toxic chemicals by these cells. Immune complex reactions can be local and may result in conditions such as, e.g., the arthus reaction or cause systemic disease such as serum sickness or some of the aspects of systemic lupus erythematous (SLE).

Type IV hypersensitivity is cell mediated and is sometimes called delayed-type hypersensitivity. Type IV hypersensitivity is mediated by T lymphocytes and often results in the formation of a granulomatous reaction. In a granulomatous reaction, a form of macrophage called an epitheloid cells attempts to, but fails, to digest an antigen. The antigen's persistence leads to the release of cytokines that attract additional lymphocytes resulting in chronic foci of inflammation. The foci have high concentrations of cytotoxic T-lymphocytes which release granzymes and performs which are toxic to adjacent cells. Type IV hypersensitivity is a prominent component of autoimmune diseases such as, e.g., Sjogren's Syndrome, Sarcoidosis, and contact dermatitis.

Pathologic states can combine different types of hypersensitivity reactions. In autoimmune diseases host antigens stimulate hypersensitivity with serious consequences for the host. For example, in SLE host antigens induce Type II reactions against blood cells while Type III reactions lead to blood vessel and renal glomerular damage. In addition, hypersensitivity reactions are also seen in iatrogenic conditions such as drug reactions and transplant rejection. Transplant rejection includes components of Type II and Type IV hypersensitivity. Accordingly, FAC water used in accordance with the invention in transplantable organs or cells could greatly reduced the possibility of being rejected by the host.

It has been found that the FAC water administered in accordance with the invention is virtually free of toxicity to normal tissues and normal mammalian cells. The FAC water administered in accordance with the invention causes no significant decrease in the viability of eukaryotic cells, no significant increase in apoptosis, no significant acceleration of cell aging and/or no significant oxidative DNA damage in mammalian cells. The non-toxicity is particularly advantageous, and perhaps even surprising, given that the disinfecting power of the FAC water administered in accordance with the invention is roughly equivalent to that of hydrogen peroxide, yet is significantly less toxic than hydrogen peroxide is to normal tissues and normal mammalian cells. These findings demonstrate that the FAC water administered in accordance with the present invention is safe for use, e.g., in mammals, including humans.

For the FAC water administered in accordance with the invention, the cell viability rate is preferably at least about 65%, more preferably at least about 70%, and still more preferably at least about 75% after an about 30 minute exposure to the FAC water. In addition, the FAC water administered in accordance with the invention preferably causes only up to about 10% of cells, more preferably only up to about 5% of cells, and still more preferably only up to about 3% of cells to expose Annexin-V on their cellular surfaces when contacted with the FAC water for up to about thirty minutes or less (e.g., after about thirty minutes or after about five minutes of contact with the FAC water).

Further, the FAC water administered in accordance with the invention preferably causes less than about 15% of cells, more preferably less than about 10% of cells, and still more preferably less than about 5% of cells to express the SA-$\beta$-galactosidase enzyme after chronic exposure to the FAC water. The FAC water administered in accordance with the invention preferably causes caused the same fraction of the oxidative DNA adduct formation caused by saline solution, e.g., less than about 20% of the oxidative DNA adduct formation, less than about 10% of the oxidative DNA adduct formation, or about 5% or less of the oxidative DNA adduct formation normally caused by hydrogen peroxide in cells treated under equivalent conditions.

The FAC water administered in accordance with the invention produces no significant RNA degradation. Accordingly, RNA extracted from human cell cultures after an about 30 minutes exposure to the FAC water or at about 3 hours after an about 30 minute-exposure and analyzed by denaturing gel electrophoresis, will typically show no significant RNA degradation and will typically exhibit two discreet bands corresponding to the ribosomal eukaryotic RNAs (i.e. 28S and 18S) indicating that the FAC water administered in accordance with the invention leaves the RNA substantially intact. Similarly, RNA extracted from human cell cultures after about 30 minutes of exposure to the FAC water or after about 3 hours of exposure, can be subjected reverse transcription and amplification (RT-PCR) of the constitutive human GAPDH (Glyceraldehyde-3-phosphate dehydrogenase) gene and result in a strong GAPDH band on gel electrophoresis of the RT-PCR products. By contrast, cells treated with HP for a similar period show significant RNA degradation and little if any GAPDH RT-PCR product.

The FAC water used in accordance with the present invention can be administered using any suitable method of administration known in the art. For instance, the FAC water can be administered parenterally, endoscopically or directly to the surface of any affected biological tissue, e.g., to the skin and/or one or more mucosal surfaces. Parenteral administration can include using, for example, administering the FAC water intramuscularly, subcutaneously, intravenously, intra-arterially, intrathecally, intravesically or into a synovial space. Endoscopic administration of the FAC water can include using, e.g., bronchoscopy, colonoscopy, sigmoidoscopy, hysterscopy, laparoscopy, arthroscopy, gastroscopy or a transurethral approach. Administering the FAC water to a mucosal surface can include, e.g., administration to a nasal, oral, tracheal, bronchial, esophageal, gastric, intestinal, peritoneal, urethral, vesicular, urethral, vaginal, uterine, fallopian, and synovial mucosal surface. Parenteral administration also can include administering the FAC water used in accordance with the invention intravenously, subcutaneously, intramuscularly, or intraperitoneally.

The FAC water used in accordance with the invention can be administered topically, e.g., as a liquid, spray, mist, aerosol or steam by any suitable process, e.g., by aerosolization, nebulization or atomization. The FAC solution of the present invention can be administered to the upper airway as a steam or a spray. When the FAC water is administered by aerosolization, nebulization or atomization, it is preferably administered in the form of droplets having a diameter in the range of from about 0.1 micron to about 100 microns, preferably from about 1 micron to about 10 microns. In one embodiment, the method of the present invention includes administering the FAC water in the form of droplets having a diameter in the range of from about 1 micron to about 10 microns to one or more mucosal tissues, e.g., one or more upper respiratory tissues and/or lung tissues.

Methods and devices, which are useful for aerosolization, nebulization and atomization, are well known in the art. Medical nebulizers, for example, have been used to deliver a metered dose of a physiologically active liquid into an inspiration gas stream for inhalation by a recipient. See, e.g., U.S. Pat. No. 6,598,602. Medical nebulizers can operate to generate liquid droplets, which form an aerosol with the inspiration gas. In other circumstances medical nebulizers may be used to inject water droplets into an inspiration gas stream to provide gas with a suitable moisture content to a recipient, which is particularly useful where the inspiration gas stream is provided by a mechanical breathing aid such as a respirator, ventilator or anesthetic delivery system.

An exemplary nebulizer is described, for example, in WO 95/01137, which describes a hand held device that operates to eject droplets of a medical liquid into a passing air stream (inspiration gas stream), which is generated by a recipient's inhalation through a mouthpiece. Another example can be found in U.S. Pat. No. 5,388,571, which describes a positive-pressure ventilator system which provides control and augmentation of breathing for a patient with respiratory insufficiency and which includes a nebulizer for delivering particles of liquid medication into the airways and alveoli of the lungs of a patient. U.S. Pat. No. 5,312,281 describes an ultrasonic wave nebulizer, which atomizes water or liquid at low temperature and reportedly can adjust the size of mist. In addition, U.S. Pat. No. 5,287,847 describes a pneumatic nebulizing apparatus with scalable flow rates and output volumes for delivering a medicinal aerosol to neonates, children and adults. Further, U.S. Pat. No. 5,063,922 describes an ultrasonic atomizer. The FAC water also may be dispensed in aerosol form as part of an inhaler system for treatment of infections in the lungs and/or air passages or for the healing of wounds in such parts of the body.

For larger scale applications, a suitable device may be used to disperse the FAC water into the air including, but not limited to, humidifiers, misters, foggers, vaporizers, atomizers, water sprays, and other spray devices. Such devices permit the dispensing of the FAC water on a continuous basis. An ejector which directly mixes air and water in a nozzle may be employed. The FAC water may be converted to steam, such as low pressure steam, and released into the air stream. Various types of humidifiers may be used such as ultrasonic humidifiers, stream humidifiers or vaporizers, and evaporative humidifiers. The particular device used to disperse the FAC water may be incorporate into a ventilation system to provide for widespread application of the FAC water throughout an entire house or healthcare facility (e.g., hospital, nursing home, etc.).

In accordance with the invention, the FAC water can be administered alone or in combination with one or more pharmaceutically acceptable carriers, e.g., vehicles, adjuvants, excipients, diluents, combinations thereof, and the like, which are preferably compatible with one or more of the species that exist in the FAC water. One skilled in the art can easily determine the appropriate formulation and method for administering the FAC water used in accordance with the present invention. Any necessary adjustments in dose can be readily made by a skilled practitioner to address the nature and/or severity of the condition being treated in view of one or more clinically relevant factors, such as, e.g., side effects, changes in the patient's overall condition, and the like.

For example, the FAC water can be formulated by combining or diluting the FAC water with up to about 25% (wt./wt. or vol./vol.) of a suitable carrier, up to about 50% (wt./wt. or vol./vol.) of a suitable carrier, up to about 75% (wt./wt. or vol./vol.) of a suitable carrier, up to about 90% (wt./wt. or vol./vol.) of a suitable carrier, up to about 95% (wt./wt. or vol./vol.) of a suitable carrier, or even with up to about 99% (wt./wt. or vol./vol.) or more of a suitable carrier. Suitable carriers can include, e.g., water (e.g., distilled water, sterile water, e.g., sterile water for injection, sterile saline and the like). Suitable carriers also can include one or more carriers described in U.S. patent application Ser. No. 10/916,278. Exemplary formulations can include, e.g., solutions in which the FAC water is diluted with sterile water or sterile saline, wherein the FAC water is diluted by up to about 25% (vol./vol.), by up to about 50% (vol./vol.), by up to about 75% (vol./vol.), by up to about 90% (vol./vol.), by up to about 95% (vol./vol.), or by up to 99% (vol./vol.) or more of a suitable carrier.

The FAC water administered in accordance with the invention can further be combined with (or be administered in conjunction with) one or more additional therapeutic agents, e.g., one or more active compounds selected from the group consisting of antibacterial agents (e.g., antibiotics), anti-viral agents, anti-inflammatory agents, and combinations thereof.

The therapeutically effective amount administered to the patient, e.g., a mammal, particularly a human, in the context of the present invention should be sufficient to affect a therapeutic or prophylactic response in the patient over a reasonable time frame. The dose can be readily determined using methods that are well known in the art. One skilled in the art will recognize that the specific dosage level for any particular patient will depend upon a variety of potentially therapeutically relevant factors. For example, the dose can be determined based on the strength of the particular FAC water employed, the severity of the condition, the body weight of the patient, the age of the patient, the physical and mental condition of the patient, general health, sex, diet, the frequency of applications, and the like. The size of the dose also can be determined based on the existence, nature, and extent of any adverse side effects that might accompany the administration of a particular FAC water. It is desirable, whenever possible, to keep adverse side effects to a minimum.

Factors, which can be taken into account for a specific dosage can include, for example, bioavailability, metabolic profile, time of administration, route of administration, rate of excretion, the pharmacodynamics associated with a particular FAC water in a particular patient, and the like. Other factors can include, e.g., the potency or effectiveness of the FAC water with respect to the particular condition to be treated, the severity of the symptoms presented prior to or during the course of therapy, and the like. In some instances, what constitutes a therapeutically effective amount also can be determined, in part, by the use of one or more of the assays, e.g., bioassays, which are reasonably clinically predictive of the efficacy of a particular FAC water for the treatment or prevention of a particular condition.

The FAC water used in accordance with the present invention can be administered, alone or in combination with one or more additional therapeutic agents, to a patient, e.g., a human, e.g., to treat an existing condition. The FAC water of the present invention also can be administered prophylactically, alone or in combination with one or more additional therapeutic agents, to a patient, e.g., a human, that has been exposed to one or more causative agents associated with the condition. For example, the FAC water can be suitably administered prophylactically to a patient that has been exposed to one or more inflammation-causing microorganisms (e.g., biofilm associated bacteria and/or fungi)— or hypersensitivity epitope or allergen—to inhibit or decrease the likelihood of inflammation (and even infection) associated with the microorganism or epitope in a patient, or decrease the severity of an inflammation (and even infection or allergy) that develops as a result of such exposure.

One skilled in the art will appreciate that suitable methods of administering the FAC water used in accordance with the present invention are available, and, although more than one route of administration can be used, a particular route can provide a more immediate and more effective reaction than another route. The therapeutically effective amount can be the dose necessary to achieve an "effective level" of the FAC water in an individual patient, independent of the number of applications a day. The therapeutically effective amount can be defined, for example, as the amount required to be administered to an individual patient to achieve a blood level, tissue level, and/or intracellular level of the FAC water (or one or more active species contained therein) to prevent or treat the condition in the patient.

When the effective level is used as a preferred endpoint for dosing, the actual dose and schedule can vary depending, for example, upon inter-individual differences in pharmacokinetics, distribution, metabolism, and the like. The effective level also can vary when the FAC water is used in combination with one or more additional therapeutic agents, e.g., one or more anti-infective agents, one or more "moderating," "modulating" or "neutralizing agents," e.g., as described in U.S. Pat. Nos. 5,334,383 and 5,622,848, one or more anti-inflammatory agents, and the like.

An appropriate indicator can be used for determining and/or monitoring the effective level. For example, the effective level can be determined by direct analysis (e.g., analytical chemistry) or by indirect analysis (e.g., with clinical chemistry indicators) of appropriate patient samples (e.g., blood and/or tissues). The effective level also can be determined, for example, by direct or indirect observations such as, e.g., the concentration of urinary metabolites, changes in markers associated with the condition (e.g., viral count in the case of a viral infection), histopathology and immunochemistry analysis, positive changes in image analysis (e.g. X ray, CT scan, NMR, PET, etc), nuclear medicine studies, decrease in the symptoms associated with the conditions, and the like.

Methods in accordance with the invention include the sterilization of and reduction in the incidence of infections associated with implanted medical devices such as, e.g., epicardial leads, cardiac and cerebral pacemakers, defibrillators, left ventricular assist devices, mechanical heart valves, total artificial hearts, ventriculoatrial shunts, pledgets, patent ductus arteriosus occlusion devices (plugs, double umbrellas, buttons, discs, embolization coils), atrial septal defect and ventricular septal defect closure devices (bard clamshell occluders, discs, buttons, double umbrellas), conduits, patches, peripheral vascular stents, coronary artery stents, vascular grafts, abdominal mesh reinforcements, hemodialysis shunts, intra-aortic balloon pumps, angioplasty balloon catheters, angiography catheters, vena caval filters, endotracheal tubes, cochlear implants, tympanostomy tubes, bioabsorbable osteoconductive drug-releasing hard tissue fixation devices, artificial joint replacements and other orthopedic implants. Further, methods in accordance with the invention can be used to sterilize or reduce the incidence of infections associated with medical devices that are not fully implanted such as, e.g., contact lenses, intrauterine devices, dental and orthodontic appliances and fixtures, urinary catheters, intravenous catheters, sutures and surgical staples.

The FAC water may be dispensed, impregnated, coated, covered or otherwise applied to the medical device by any suitable method. For example, individual portions of medical device may be treated with a discrete amount of the FAC water. The medical device or its components may be dipped in, soaked in or sprayed with the FAC water. The FAC water may be contacted, come into physical contact with, the medical device for any suitable time period provided that the contact results in an at least about a 3 log reduction in biofilm bacteria concentration, preferably an at least about a 3.5 log reduction in biofilm bacteria concentration, more preferably an at least about a 4 log reduction in biofilm bacteria concentration, even more preferably an at least about a 5 log reduction in biofilm bacteria concentration, and most preferably an at least about a 6 log reduction in biofilm bacteria concentration within 30 minutes. Accordingly, suitable contact times include at least about 10 seconds, at least about 30 seconds, at least 1 minute, at least about 5 minutes, at least about 10 minutes, at least about 20 minutes, at least about 30 minutes, at least about 1 hour, at least about 2 hours, at least about 3 hours, at least about 4 hours, at least about 12 hour, at least about 24 hour, at least about 2 days, at least about 3 days, at least about 5 days, and about 1 week.

The FAC water used to contact the medical device can be at any suitable temperature including, e.g., room temperature, 37° C. or ≥100° C. Further, the FAC water used to contact the medical device may also be comprised of any suitable antimicrobial, including, e.g., bleaches, antifungals, antibiotics, antivirals, disinfectant salts, alcohols or biologics.

If the medical device has a web structure, a mass treatment of a continuous web of medical device material with the FAC water is carried out. The entire web of medical device material may be soaked in the FAC water. Alternatively, as the medical device web is spooled, or even during creation of a nonwoven substrate, the FAC water is sprayed or metered onto the web.

For small scale applications to a medical, the FAC water may be dispensed through a spray bottle that includes a standpipe and pump. Alternatively, the FAC water may be packaged in aerosol containers. Aerosol containers generally include the product to be dispensed, propellant, container, and valve. The valve includes both an actuator and dip tube. The contents of the container are dispensed by pressing down on the actuator. The various components of the aerosol container are compatible with the FAC water. Suitable propellants may include a liquefied halocarbon, hydrocarbon, or halocarbon-hydrocarbon blend, or a compressed gas such as carbon dioxide, nitrogen, or nitrous oxide. Aerosol systems typically yield droplets that range in size from about 0.15 μm to about 5 μm.

Conventional FAC waters have an extremely limited shelf-life, usually only a few hours. As a result of this short lifespan, using conventional FAC waters requires the production to take place in close proximity to the point of use. From a practical standpoint, this means that the facility, e.g., a healthcare facility such as a hospital, must purchase, house and maintain the equipment necessary to produce conventional FAC water. Additionally, conventional manufacturing techniques have not been able to produce sufficient commercial-scale quantities to permit widespread use, e.g., as a general disinfecting agent for healthcare facilities.

Unlike conventional FAC waters, the FAC water administered in accordance with the invention is stable for at least about twenty-hours after its preparation. In addition, the FAC water administered in accordance with the invention is generally environmentally safe and, thus, avoids the need for costly disposal procedures. Preferably, the FAC water administered in accordance with the invention is stable for at least about one week (e.g., one week, two weeks, three weeks, four weeks or more), and more preferably at least about two months. Still more preferably, the FAC water administered in accordance with the invention is stable for at least about six months. Even more preferably, the FAC water administered in accordance with the invention is stable for at least about one year, and most preferably is stable for more than about one year, e.g., at least about two years or at least about three years.

Stability can be measured based on the ability of the FAC water to remain suitable for one or more uses, for example, decontamination, disinfection, sterilization, anti-microbial cleansing, and wound cleansing, for a specified period of time after its preparation under normal storage conditions (e.g., room temperature). The stability of the FAC water administered in accordance with the invention also can be measured by storage under accelerated conditions, e.g., from about 30° C. to about 60° C., in which the FAC water preferably is stable for up to about 90 days, and more preferably for up to about 180 days.

Stability also can be measured based on the concentration over time of one or more species (or precursors thereof) present in solution during the shelf-life of the FAC water. Preferably, the concentrations of one or more species, e.g., hypochlorous acid and sodium hypochlorite, are maintained at about 70% or greater of their initial concentration for at least about two months after preparation of the FAC water. More preferably, the concentration of one of more of these species is maintained at about 80% or greater of their initial concentration for at least about two months after preparation of the FAC water. Still more preferably, the concentration of one or more of such species is maintained at about 90% or greater, and most preferably is maintained at about 95% or greater, of their initial concentration for at least about two months after preparation of the FAC water.

Stability also can be determined based on the reduction in the amount of organisms present in a sample following exposure to the FAC water. Measuring the reduction of organism concentration can be made on the basis of any suitable organism including, e.g., bacteria, fungi, yeasts, or viruses. Suitable organisms can include, e.g., *Escherichia coli, Staphylococcus aureus, Candida albicans*, and *Bacillus athrophaeus* (formerly *B. subtilis*).

The FAC water administered in accordance with the invention can function as a low-level disinfectant capable of a four log ($10^4$) reduction in the concentration of live microorganisms, and also can function as a high-level disinfectant capable of a six log ($10^6$) reduction in concentration of live microorganisms. Preferably, the FAC water administered in accordance with the invention is capable of yielding at least about a four log ($10^4$) reduction in total organism concentration, following exposure for one minute when measured at least about two months after preparation of the solution. More preferably, the FAC water is capable of a $10^4$-$10^6$ reduction of organism concentration when measured at least about six months after preparation of the solution. Still more preferably, the FAC water is capable of a $10^4$-$10^6$ reduction of organism concentration when measured at least about one year after preparation of the FAC water, and most preferably when measured more than about one year, e.g., at least about two years or at least about three years, after preparation of the FAC water.

For instance, the FAC water administered in accordance with the present invention can be capable of at least about a five log ($10^5$) reduction in the concentration of a sample of live microorganisms from the group consisting of *Pseudomonas aeruginosa, Escherichia coli, Enterococcus hirae, Acinetobacter baumannii, Acinetobacter* species, *Bacteroides fragilis, Enterobacter aerogenes, Enterococcus faecalis, Vancomycin resistant-Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, Streptococcus pyogenes, Candida albicans* within thirty seconds of exposure, when measured at least two months after preparation of the FAC water (BioSciences Labs, Montana, US). Preferably, the FAC water is capable of achieving a $10^5$ reduction of all these organisms when measured at least about six months after preparation, and more preferably when measured at least about one year after preparation.

In one embodiment, the FAC water administered in accordance with the invention can reduce a sample of live microorganisms including, but not limited to, *Escherichia coli, Pseudomonas aeruginosa, Staphylococcus aureus* and *Candida albicans*, from an initial concentration of between about $1\times10^6$ and about $1\times10^8$ organisms/ml to a final concentration of about zero organisms/ml within about one minute of exposure when measured at least about two months after preparation of the FAC water. This corresponds to from about a six log ($10^6$) to about an eight log ($10^8$) reduction in organism concentration. Preferably, the FAC water is capable of achieving a $10^6$-$10^8$ reduction of *Escherichia coli, Pseudomonas aeruginosa, Staphylococcus aureus* or *Candida albicans* organisms when measured at least about six months after preparation, and more preferably when measured at least about one year after preparation.

Alternatively, the FAC water administered in accordance with the present invention can produce about a six log ($10^6$) reduction in the concentration of a spore suspension of *Bacillus athrophaeus* spores within about five minutes of exposure when measured at least about two months after preparation of the FAC water. Preferably, the FAC water administered in accordance with the invention can achieve about a $10^6$ reduction in the concentration of *Bacillus athrophaeus* spores when measured at least about six months after preparation, and more preferably when measured at least about one year after preparation.

The FAC water administered in accordance with the invention also can produce about a four log ($10^4$) reduction in the concentration of a spore suspension of *Bacillus athrophaeus* spores within about thirty (30) seconds of exposure when measured at least about two months after preparation of the FAC water. Preferably, the FAC water can achieve this reduction in the concentration of *Bacillus athrophaeus* spores when measured at least about six months after preparation, and more preferably when measured, at least about one year after preparation.

The FAC water administered in accordance with the invention further can produce about a six log ($10^6$) reduction in the concentration of fungal spores, such as *Aspergillis niger* spores, within about five to about ten minutes of exposure when measured at least about two months after preparation of the FAC water. Preferably, the FAC water can achieve a $10^6$ reduction in the concentration of fungal spores when measured at least about six months after preparation, and more preferably when measured at least about one year after preparation.

FAC water typically includes, but is not limited to, hypochlorous acid (HClO), hypochlorite ions (ClO$^-$), sodium hypochlorite (NaOCl), and precursors thereof. The ratio of hypochlorous acid to hypochlorite ion in the FAC water is dependent upon pH. At a pH of 7.4, the concentration of hypochlorous acid is approximately 50% of the total FAC. At a lower pH range (e.g., from about 4.5 to about 6.0), the concentration of hypochlorous acid is substantially all of the total FAC. Temperature also impacts the ratio of hypochlorous acid to hypochlorite ion.

The total concentration of oxychlorine species present in the FAC water is generally at least about 30 mg/mL and preferably from about 30 mg/L to about 400 mg/L. More preferably, the total concentration of oxychlorine species is from about 50 mg/L to about 200 mg/L, and most preferably from about 150 mg/L to about 200 mg/L.

The chlorine content of the FAC water may be measured by methods known in the art, such as the DPD colorimeter method (Lamotte Company, Chestertown, Md.) or other known methods such as, e.g., methods established by the Environmental Protection Agency. In the DPD colorimeter method, a yellow color is formed by the reaction of free chlorine with N,N-diethyl-p-phenylenediamine (DPD) and the intensity is measured with a calibrated calorimeter that provides the output in parts per million. Further addition of potassium iodide turns the solution a pink color to provide the total chlorine value. The amount of bound chlorine present is then determined by subtracting free chlorine from the total chlorine.

In one embodiment, the FAC water administered in accordance with the invention comprises one or more oxychlorine species. The oxychlorine species can include one or more species selected from the group consisting of hypochlorous acid (HOCl), hypochlorite ions (OCl$^-$), sodium hypochlorite (NaOCl), precursors thereof and mixtures thereof. The FAC water may optionally include one or more free chlorine species in addition to oxychlorine species. Suitable free chlorine species include dissolved chlorine gas (Cl$_2$).

In one embodiment, the FAC water includes one or more oxychlorine species or one or more precursors thereof, and is stable for at least about 24 hours, preferably for at least about one week, more preferably for at about least two months, and still more preferably for at least about six months after its preparation. Even more preferably, such FAC water is stable for at least about one year, and most preferably for more than about one year, e.g., at least about two years or at least about three years.

It is also preferred that the FAC water of the invention includes one or more oxychlorine species (e.g., hypochlorous acid and sodium hypochlorite) or one or more precursors thereof and has a pH of from about 4.5 to about 7.7. In one embodiment, the pH of the FAC water is preferably about 4.5 to about 6.0. In another embodiment, the pH is preferably from about 6.8 to about 7.6, more preferably from about 7.0 to about 7.5, most preferably from about 7.3 to about 7.5.

An exemplary FAC water administered in accordance with the present invention can comprise at least about 30 mg/mL total free available chlorine including, for example, from about 150 mg/L to about 200 mg/L total free available chlorine, and can be stable for at least about one week, e.g., at least about two months, at least about six months, at least about one year, or more than about one year, e.g., at least about two years or at least about three years.

While in no way limiting the present invention, it is believed that the control of pH and other variables (e.g., salinity) can provide stable FAC waters, which contain one or more oxychlorine species or precursors thereof, such as for example, hypochlorous acid The FAC waters administered in accordance with the invention preferably comprises one or more oxidized water species which can yield free radicals (such as, e.g., hydroxyl radicals) on exposure to iron.

Accordingly, combinations of these factors can characterize the FAC water for use in accordance with the invention, for example, the wherein the pH of the FAC water is from about 4.5 to about 7.7 and the concentration of oxychlorine species in the FAC water is from about 30 mg/L to about 200 mg/L.

The FAC water administered in accordance with the present invention can be produced by any suitable method including, for example, an oxidation-reduction process. In such an electrolytic process (also known as a redox reaction), electrical energy is used to produce one or more chemical changes in an aqueous solution. Exemplary electrolysis processes for preparing suitable FAC waters are described, e.g., in U.S. Patent Application Publication Nos. US 2005/0139808 and US 2005/0142157.

In the electrolytic process, electrical energy is introduced into and transported through water by the conduction of electrical charge from one point to another in the form of an electrical current. In order for the electrical current to arise and subsist there should be charge carriers in the water, and there should be a force that makes the carriers move. The charge carriers can be electrons, as in the case of metal and semiconductors, or they can be positive and negative ions in the case of solutions. A reduction reaction occurs at the cathode while an oxidation reaction occurs at the anode. At least some of the reductive and oxidative reactions that are believed to occur are described in International Application WO 03/048421 A1.

As used herein, water produced at an anode is referred to as anode water and water produced at a cathode is referred to as cathode water. Anode water typically contains oxidized species produced from the electrolytic reaction while cathode water typically contains reduced species from the reaction. Anode water generally has a low pH, typically of from about 1 to about 6.8. The anode water preferably contains chlorine in various forms including, for example, chlorine gas, chloride ions, hydrochloric acid and/or hypochlorous acid, or one or more precursors thereof. Oxygen in various forms is also preferably present including, for example, oxygen gas, and possibly one or more species formed during production (e.g., peroxides, and/or ozone), or one or more precursors thereof. Cathode water generally has a high pH, typically from about 7.2 to about 11. Cathode water can contain hydrogen gas, hydroxyl radicals, and/or sodium ions.

The FAC water administered in accordance with the invention can include a mixture of anode water (e.g., water produced in the anode chamber of an electrolytic cell) and cathode water (e.g., water produced in the cathode chamber of an electrolysis cell). Preferably, the FAC water administered in accordance with the present invention contains cathode water, e.g., in an amount of from about 10% by volume to about 90% by volume of the solution. More preferably, cathode water is present in the FAC water in an amount of from about 10% by volume to about 50% by volume, and still more preferably of from about 20% by volume to about 40% by volume of the solution, e.g., from about 20% by volume to about 30% by volume of the solution. Additionally, anode water can be present in the FAC water, e.g., in an amount of from about 50% by volume to about 90% by volume of the solution. Exemplary FAC water can contain from about 10% by volume to about 50% by volume of cathode water and from about 50% by volume to about 90% by volume of anode water. The anode and cathode water can be produced using the three-chambered electrolysis cell shown in FIG. 1.

The FAC water administered in accordance with the invention is preferably produced using at least one electrolysis cell comprising an anode chamber, a cathode chamber and a salt solution chamber located between the anode and cathode chambers, wherein at least some of the anode and cathode water are combined such that the FAC water comprises anode water and cathode water. A diagram of an exemplary three chamber electrolysis cell that can be used in preparing an exemplary FAC water is shown in FIG. 1.

The electrolysis cell 100 has an anode chamber 102, cathode chamber 104 and salt solution chamber 106. The salt solution chamber is located between the anode chamber 102 and cathode chamber 104. The anode chamber 102 has an inlet 108 and outlet 110 to permit the flow of water through the anode chamber 100. The cathode chamber 104 similarly has an inlet 112 and outlet 114 to permit the flow of water through the cathode chamber 104. The salt solution chamber 106 has an inlet 116 and outlet 118. The electrolysis cell 100 preferably includes a housing to hold all of the components together.

The anode chamber 102 is separated from the salt solution chamber by an anode electrode 120 and an anion ion exchange membrane 122. The anode electrode 120 may be positioned adjacent to the anode chamber 102 with the membrane 122 located between the anode electrode 120 and the salt solution chamber 106. Alternatively, the membrane 122 may be positioned adjacent to the anode chamber 102 with the anode electrode 120 located between the membrane 122 and the salt solution chamber 106.

The cathode chamber 104 is separated from the salt solution chamber by a cathode electrode 124 and a cathode ion exchange membrane 126. The cathode electrode 124 may be positioned adjacent to the cathode chamber 104 with the membrane 126 located between the cathode electrode 124 and the salt solution chamber 106. Alternatively, the membrane 126 may be positioned adjacent to the cathode chamber 104 with the cathode electrode 124 located between the membrane 126 and the salt solution chamber 106.

The electrodes preferably are constructed of metal to permit a voltage potential to be applied between the anode chamber and cathode chamber. The metal electrodes are generally planar and have similar dimensions and cross-sectional surface area to that of the ion exchange membranes. The electrodes are configured to expose a substantial portion of the surface of the ion exchange members to the water in their respective anode chamber and cathode chamber. This permits the migration of ionic species between the salt solution chamber, anode chamber and cathode chamber. Preferably, the electrodes have a plurality of passages or apertures evenly spaced across the surface of the electrodes.

A source of electrical potential is connected to the anode electrode 120 and cathode electrode 124 so as to induce an oxidation reaction in the anode chamber 102 and a reduction reaction in the cathode chamber 104.

The ion exchange membranes 122 and 126 used in the electrolysis cell 100 may be constructed of any suitable material to permit the exchange of ions between the salt solution chamber 106 and the anode chamber 102 such as, e.g., chloride ions ($Cl^-$) and between the salt solution salt solution chamber 106 and the cathode chamber 104 such as, e.g., sodium ions ($Na^+$). The anode ion exchange membrane 122 and cathode ion exchange membrane 126 may be made of the same or different material of construction. Preferably, the anode ion exchange membrane comprises a fluorinated polymer. Suitable fluorinated polymers include, for example, perfluorosulfonic acid polymers and copolymers such as perfluorosulfonic acid/PTFE copolymers and perfluorosulfonic acid/TFE copolymers. The ion exchange membrane may be constructed of a single layer of material or multiple layers. Suitable ion exchange membrane polymers can include one or more ion exchange membrane polymers marketed under the trademark Nafion®.

The source of the water for the anode chamber 102 and cathode chamber 104 of the electrolysis cell 100 may be any suitable water supply. The water may be from a municipal water supply or alternatively pretreated prior to use in the electrolysis cell. Preferably, the water is pretreated and is selected from the group consisting of softened water, purified water, distilled water, and deionized water. More preferably, the pretreated water source is ultrapure water obtained using reverse osmosis purification equipment.

The salt water solution for use in the salt water chamber 106 can include any aqueous salt solution that contains suitable ionic species to produce the FAC water. Preferably, the salt water solution is an aqueous sodium chloride (NaCl) salt solution, also commonly referred to as a saline solution. Other suitable salt solutions can include other chloride salts such as potassium chloride, ammonium chloride and magnesium chloride as well as other halogen salts such as potassium and bromine salts. The salt solution can contain a mixture of salts.

The salt solution can have any suitable concentration. For example, the salt solution can be saturated or concentrated. Preferably, the salt solution is a saturated sodium chloride solution.

Figure 2:
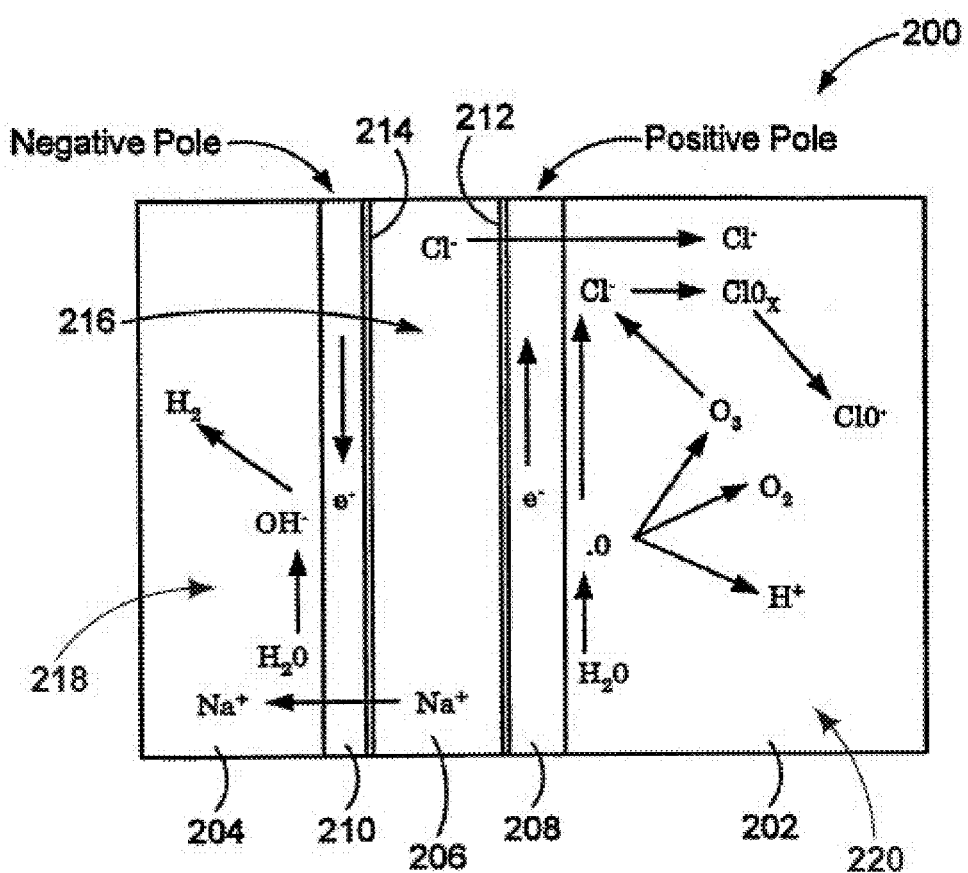
FIG. 2 illustrates a three-chambered electrolysis cell and depicts ionic species that are believed to be generated during the production process.

FIG. 2 illustrates what are believed to be various ionic species produced in the three chambered electrolysis cell useful in connection with the invention. The three chambered electrolysis cell 200 includes an anode chamber 202, cathode chamber 204, and a salt solution chamber 206. Upon application of a suitable electrical current to the anode 208 and cathode 210, the ions present in the salt solution flowing through the salt solution chamber 206 migrate through the anode ion exchange membrane 212 and cathode ion exchange membrane 214 into the water flowing through the anode chamber 202 and cathode chamber 204, respectively.

Positive ions migrate from the salt solution 216 flowing through the salt solution chamber 206 to the cathode water 218 flowing through the cathode chamber 204. Negative ions migrate from the salt solution 216 flowing through the salt solution chamber 206 to the anode water 220 flowing through the anode chamber 202.

Preferably, the salt solution 216 is aqueous sodium chloride (NaCl), which contains both sodium ions (Na$^+$) and chloride ions (Cl$^-$) ions. Positive Na$^+$ ions migrate from the salt solution 216 to the cathode water 218. Negative Cl$^-$ ions migrate from the salt solution 216 to the anode water 220.

The sodium ions and chloride ions may undergo further reaction in the anode chamber 202 and cathode chamber 204. For example, chloride ions can react with various oxygen ions and other species (e.g., oxygen containing free radicals, $O_2$, $O_3$) present in the anode water 220 to produce ClOn− and ClO$^-$. Other reactions may also take place in the anode chamber 202 including the formation of oxygen free radicals, hydrogen ions (H$^+$), oxygen (e.g., as $O_2$), ozone ($O_3$), and peroxides. In the cathode chamber 204, hydrogen gas ($H_2$), sodium hydroxide (NaOH), hydroxide ions (OH$^-$), and other radicals may be formed.

Figure 3:
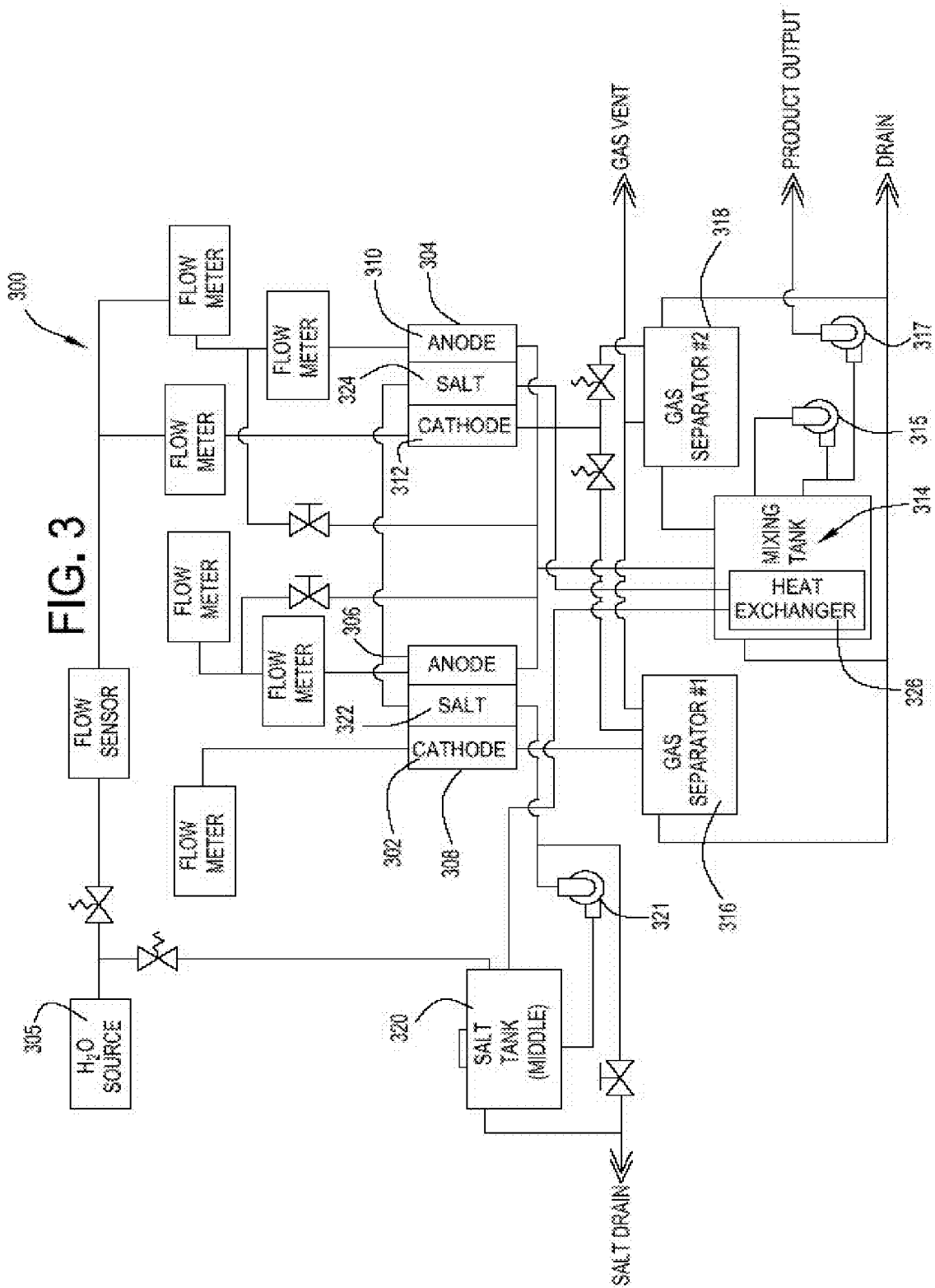
FIG. 3 is a schematic flow diagram of a process for producing an exemplary FAC water.

The apparatus for producing the FAC water also can be constructed to include at least two three chambered electrolysis cells. Each of the electrolytic cells includes an anode chamber, cathode chamber, and salt solution chamber separating the anode and cathode chambers. The apparatus includes a mixing tank for collecting the anode water produced by the electrolytic cells and a portion of the cathode water produced by one or more of the electrolytic cells. Preferably, the apparatus further includes a salt recirculation system to permit recycling of the salt solution supplied to the salt solution chambers of the electrolytic cells. A diagram of an exemplary process for producing an FAC water using two electrolysis cells is shown in FIG. 3.

The process 300 includes two three-chambered electrolytic cells, specifically a first electrolytic cell 302 and second electrolytic cell 304. Water is transferred, pumped or otherwise dispensed from the water source 305 to anode chamber 306 and cathode chamber 308 of the first electrolytic cell 302 and to anode chamber 310 and cathode chamber 312 of the second electrolytic cell 304. Advantageously, this process can produce from about 1 liter/minute to about 50 liters/minute of FAC water. The production capacity may be increased by using additional electrolytic cells. For example, three, four, five, six, seven, eight, nine, ten or more three-chambered electrolytic cells may be used to increase the output of the FAC water administered in accordance with the invention.

The anode water produced in the anode chamber 306 and anode chamber 310 are collected in the mixing tank 314. A portion of the cathode water produced in the cathode chamber 308 and cathode chamber 312 is collected in mixing tank 314 and combined with the anode water. The remaining portion of cathode water produced in the process is discarded. The cathode water may optionally be subjected to gas separator 316 and/or gas separator 318 prior to addition to the mixing tank 314. The gas separators remove gases such as hydrogen gas that are formed in cathode water during the production process.

The mixing tank 314 may optionally be connected to a recirculation pump 315 to permit homogenous mixing of the anode water and portion of cathode water from electrolysis cells 302 and 304. Further, the mixing tank 314 may optionally include suitable devices for monitoring the level and pH of the FAC water. The FAC water may be transferred from the mixing tank 314 via pump 317 for application in disinfection or sterilization at or near the location of the mixing tank. Alternatively, the FAC water may be dispensed into one or more suitable containers for shipment to a remote site (e.g., warehouse, hospital, etc.).

The process 300 further includes a salt solution recirculation system to provide the salt solution to salt solution chamber 322 of the first electrolytic cell 302 and the salt solution chamber 324 of the second electrolytic cell 304. The salt solution is prepared in the salt tank 320. The salt is transferred via pump 321 to the salt solution chambers 322 and 324. Preferably, the salt solution flows in series through salt solution chamber 322 first followed by salt solution chamber 324. Alternatively, the salt solution may be pumped to both salt solution chambers simultaneously.

Before returning to the salt tank 320, the salt solution may flow through a heat exchanger 326 in the mixing tank 314 to control the temperature of the FAC water as needed.

The ions present in the salt solution are depleted over time in the first electrolytic cell 302 and second electrolytic cell 304. An additional source of ions periodically can be added to the mixing tank 320 to replace the ions that are transferred to the anode water and cathode water. The additional source of ions may be used, e.g., to maintain a constant pH of the salt solution, which can to drop (i.e., become acidic) over time. The source of additional ions may be any suitable compound including, for example, salts such as, e.g., sodium chloride. Preferably, sodium hydroxide is added to the mixing tank 320 to replace the sodium ions (Na⁺) that are transferred to the anode water and cathode water.

In another embodiment, the FAC water of the present invention can be produced by a chemical process wherein chlorine is added to a buffer solution comprising a buffering agent and water.

The source of the water for the chemical process may be any suitable water supply. The water may be from a municipal water supply or alternatively pretreated prior to use in the electrolysis cell. Preferably, the pretreated water is selected from the group consisting of softened water, purified water, distilled water, and deionized water. More preferably, the pretreated water source is ultrapure water obtained using reverse osmosis purification equipment.

The chlorine can be added to the buffer solution in any suitable form. For example, the chlorine can be added to the buffer solution as an aqueous solution or a gas. Preferably, the chlorine is added to the buffer solution as a gas. Similarly, the chlorine can be added by any suitable means. Exemplary means for adding chlorine to the buffer solution include, for example, continuous spraying and bubbling. Most preferably, chlorine gas is bubbled into the buffer solution. Chlorine can be added to the buffer solution in any suitable amount and rate such that the desired pH and component content (e.g., free available chlorine) are obtained.

Following its preparation, the FAC water can be transferred to one or more suitable containers, e.g., a sealed container for distribution and sale to end users such as, e.g., health care facilities including, e.g., hospitals, nursing homes, doctor offices, outpatient surgical centers, dental offices, and the like. Suitable containers can include, e.g., a sealed container that maintains the sterility and stability of the FAC water held by the container. The container can be constructed of any material that is compatible with the FAC water. Preferably, the container is generally non-reactive with species present in the FAC water.

Preferably, the container is constructed of plastic or glass. The plastic can be rigid so that the container is capable of being stored on a shelf. Alternatively, the container can be flexible, e.g., a container made of flexible plastic such as, e.g., a flexible bag.

Suitable plastics can include, e.g., polypropylene, polyester terephthalate (PET), polyolefin, cycloolefin, polycarbonate, ABS resin, polyethylene, polyvinyl chloride, and mixtures thereof. Preferably, the container comprises one or more polyethylenes selected from the group consisting of high-density polyethylene (HDPE), low-density polyethylene (LDPE), and linear low-density polyethylene (LLDPE). Most preferably, the container is constructed of high density polyethylene.

The container preferably has an opening to permit dispensing of the FAC water. The container opening can be sealed in any suitable manner. For example, the container can be sealed with a twist-off cap or stopper. Optionally, the opening can be further sealed with a foil layer.

The headspace gas of the sealed container can be air or any other suitable gas, which preferably does not react with one or more species in the FAC water. Suitable headspace gases can include, e.g., nitrogen, oxygen, and mixtures thereof.

The FAC water administered in accordance with the invention also can be used for the prevention or treatment of an infection, e.g., by one or more infectious pathogens such as, for example, infectious microorganisms. Such microorganisms can include, for example, viruses, bacteria, and fungi. The viruses can include, e.g., one or more viruses selected from the group consisting of adenoviruses, herpes viruses, coxsackie viruses, HIV, rhinoviruses, and flu viruses. The bacteria can include, e.g., one or more bacteria selected from the group consisting of *Escherichia coli, Pseudomonas aeruginosa, Staphylococcus aureus,* and *Mycobaterium tuberculosis*. The fungi can include, e.g., one or more fungi selected from the group consisting of *Candida albicans, Bacillus subtilis* and *Bacillus athrophaeus*.

The FAC water administered in accordance with the invention also can be effective against adenovirus. Preferably, the FAC water administered in accordance with the invention preferably achieves a log-10 reduction in the adenoviral load of greater than about 2, more preferably greater than about 2.5, and still more preferably greater than about 3, after exposure to the FAC water for about 20 minutes, more preferably after exposure for about 15 minutes, and still more preferably after exposure for about 10 minutes. The FAC water administered in accordance with the invention also can be effective for reducing the viral load of HIV-1, preferably by a log reduction factor greater than about 2, more preferably by a log reduction factor of greater than about 2.5, and still more preferably by a log reduction factor of greater than about 3 after exposure to the FAC water for about five minutes.

In accordance with the method of the present invention, administering the FAC water for the prevention or treatment of infection also can serve to prevent or treat inflammation associated with the infection (or the affected tissues) as described herein.

The FAC water administered in accordance with the invention also can be used for treating impaired or damaged tissue, e.g., by contacting one or more impaired or damaged tissues with a therapeutically effective amount of the FAC water. Any suitable method can be used for contacting the impaired or damaged tissue, so as to treat the impaired or damaged tissue. For example, the impaired or damaged tissue can be treated by irrigating the tissue with the FAC water, so as to contact the impaired or damaged tissue with a therapeutically effective amount of the FAC water. The FAC water can be administered as a steam or a spray, or by aerosolization, nebulization or atomization, as described herein, so as to contact the impaired or damaged tissue with a therapeutically effective amount of the FAC water.

The FAC water administered in accordance with the invention can be used for treating tissues, which have been impaired or damaged, e.g., by surgery. For instance, the FAC water can be used for treating tissues, which have been impaired or damaged by an incision. In addition, the FAC water can be used for treating tissues, which have been impaired or damaged by oral surgery, graft surgery, implant surgery, transplant surgery, cauterization, amputation, radiation, chemotherapy, and combinations thereof. The oral surgery can include, for example, dental surgery such as, e.g., root canal surgery, tooth extraction, gum surgery, and the like.

The FAC water administered in accordance with the invention can be used for treating tissues, which have been impaired or damaged by one or more burns, cuts, abrasions, scrapes, rashes, ulcers, puncture wounds, combinations thereof, and the like, which are not necessarily caused by surgery. The FAC water administered in accordance with the invention can be used for treating impaired or damaged tissue, which is infected, or tissue impaired or damaged due to infection. Such infection can be caused by one or more infectious pathogens, such as, e.g., one or more microorganisms selected from the group consisting of viruses, bacteria, and fungi, as described herein.

In accordance with the present invention, administering the FAC water for treating impaired or damaged tissue also can serve to prevent or treat inflammation associated with the impairment or damage (or with the impaired or damaged tissue).

The FAC water administered in accordance with the invention also can be used as a disinfectant to eradicate microorganisms, including bacteria, viruses and spores, in a variety of settings, e.g., in the healthcare and medical device fields, to disinfect surfaces and medical equipment, and also can be applied in wound care, medical device sterilization, food sterilization, hospitals, consumer households and antibioterrorism. The FAC water can be used for disinfecting a surface, e.g., by contacting the surface with an anti-infective amount of the FAC water. The surface can be contacted using any suitable method. For example, the surface can be contacted by irrigating the surface with the FAC water, so as to disinfect the surface. Additionally, the surface can be contacted by applying the FAC water to the surface as a steam or a spray, or by aerosolization, nebulization or atomization, as described herein, so as to disinfect the surface. Further, the FAC water can be applied to the surface with a cleaning wipe, as described herein. By disinfecting a surface, the surface may be cleansed of infectious microorganisms. Alternatively (or additionally), the FAC water administered in accordance with the present invention can be applied to the surface to provide a barrier to infection, to thereby disinfect the surface.

The surface(s) can include one or more biological surfaces, one or more inanimate surfaces, and combinations thereof. Biological surfaces can include, for example, tissues within one or more body cavities such as, for example, the oral cavity, the sinus cavity, the cranial cavity, the abdominal cavity, and the thoracic cavity. Tissues within the oral cavity include, e.g., mouth tissue, gum tissue, tongue tissue, and throat tissue. The biological tissue also can include muscle tissue, bone tissue, organ tissue, mucosal tissue, vascular tissue, neurological tissue, and combinations thereof. Biological surfaces also include any other cultured tissue in vitro, such as primary and established cell lines, stem cells of any nature, xenotransplants, tissue substitutes (e.g. made of collagen or any other organic material in addition or not of cellular elements), any other tissue-engineered substitutes and combinations thereof.

Inanimate surfaces include, for example, implantable medical devices, prosthetic devices, and other medical devices. In accordance with the method of the present invention, the surfaces of internal organs, viscera, muscle, and the like, which may be exposed during surgery, can be disinfected, e.g., to maintain sterility of the surgical environment. In accordance with the present invention, administering the FAC water for disinfecting a surface also can serve to treat or prevent inflammation affecting one or more biological tissues associated with such surfaces.

The FAC water may also be applied to humans and/or animals to treat various conditions, including inflammation, hypersensitivity, and associated systemic effects associated with one or more of the following: surgical/open wound cleansing agent; skin pathogen disinfection (e.g., for bacteria, mycoplasmas, virus, fungi, prions); battle wound disinfection; wound healing promotion; burn healing promotion; treatment of stomach ulcers; wound irrigation; skin fungi; psoriasis; athlete's foot; pinkeye and other eye infections; ear infections (e.g., swimmer's ear); lung/nasal/sinus infections; and other medical applications on or in the human or animal body, as well as environmental remediation. The use of FAC waters as a tissue cell growth promoter is further described in U.S. Patent Application Publication 2002/0160053 A1.

The following examples further illustrate the invention but, of course, should not be construed as in any way limiting in its scope.

Materials and Methods Used in the examples 1-6

Bacterial Strains, Media and Planktonic Growth Conditions:

*P. aeruginosa* strain PAO1 and ATCC #15442 were used in this study. All strains were grown aerobically in LB medium at 37° C. in shake flasks at 250 rpm and on LB agar and Tryptic soy agar (TSA).

Neutral Free Available Chlorine Waters:

The stable neutral free available chlorine water (also known as "FAC water") herein tested was produced through the electrolysis of purified water containing limited amounts of chloride ion in a unique multi chamber cell based on the patented Microcyn™ technology. The chemically active oxychlorine species in FAC water, hypochlorous acid (HOCl) and sodium hypochlorite (NaOCl), exist in equilibrium to produce water with high efficacy against microorganisms while maintaining product stability and low toxicity. The free available chlorine content in the water used for this study was 80 mg/L (OIS-80), 125 mg/L (OIS-125) and 200 mg/L (OIS-200). All FAC water was generated at pH 7.4.

Susceptibility testing of exponential phase *P. aeruginosa* cells:

Killing of exponential phase planktonic *P. aeruginosa* cells was measured in bacterial suspensions with an initial cell density of $10^8$ CFU/ml. To do so, FAC water was added to the bacterial suspension (final concentration=0.1×FAC water) and incubated for 20 sec, 5 minutes and 20 minutes before FAC water was neutralized by diluting the bacterial suspension 10-fold into LB broth containing 0.1% sodium thiosulfate. The suspension was subsequently serially diluted and plated onto TSA. Susceptibility to bacitracin (33 U/ml) was done accordingly.

Susceptibility Testing of Stationary Phase *P. aeruginosa* Cells Using Penicylinders:

To test the susceptibility of *P. aeruginosa* to FAC water, *P. aeruginosa* was grown planktonically in LB medium to stationary phase and subsequently tested following the use-dilution method (UDM) of the Association of Official Analytical Chemists (AOAC). The bacterial suspension was standardized by dilution to meet the specification of $1.0 \times 10^4$-$5.0 \times 10^6$ CFU/carrier. Briefly, to reach these specification (highest and lowest CFU/carrier), half of the stationary phase bacterial suspensions were used undiluted to obtain ~$10^6$ CFU/carrier while the other half was diluted to obtain ~$10^4$ CFU/carrier. Stainless steel penicylinders were used as carriers. The carriers were pre-soaked overnight in 1.0 N NaOH, washed in water until rinse water was neutral to phenolphthalein, and autoclaved in 0.1% asparagine. Sterile penicylinders were immersed for 15 minutes in standardized *P. aeruginosa* broth culture, at a ratio of 1 carrier per 1.0 ml broth. The penicylinders were dried on sterile filter paper at 37° C. for 30 minutes before use. A total of 60 inoculated and dried carriers were then individually transferred by hook needle at staggered intervals to individual tubes containing 10 ml FAC water. Following exposure for 10 minutes at 20° C., each exposed carrier was transferred by hook needle at identical staggered intervals to 10 ml of LB broth with 0.1% sodium thiosulfate to neutralize FAC water. The neutralized subcultures were incubated for 48 hours at 37° C., and subsequently examined for the presence or absence of growth. This test was conducted in duplicate using different lots of FAC water.

A viability control and a carrier population control were used as positive controls. For the viability control, inoculated carrier was added directly to the growth medium. For the carrier population control, inoculated carriers were added at a ratio of 1 carrier to 10 ml of neutralizing broth, mixed, serial diluted and spread plated onto TSA. Following incubation, the CFU/carrier was determined.

To ensure proper sterilization of carriers, the sterility of the carrier was determined by incubating the carrier following autoclaving in growth medium. The carrier was considered to be sterile when no growth was observed upon incubation for 48 hours at 37° C. To confirm proper neutralization of FAC water, sterile carriers were exposed to FAC water and then transferred to 10 ml of LB broth containing 0.1% sodium thiosulfate. The growth medium was then inoculated with <100 CFU of $P.$ $aeruginosa$, incubated as described above and examined for the presence or absence of growth.

Biofilm Formation Using A Continuous Flow Tube Reactor:

Biofilms were grown as previously described. Briefly, biofilms were grown on the interior surfaces of 1 cm long, size 13 Masterflex silicone tubing (total interior volume, 1 ml; flow rate, 0.1 ml, Cole Parmer Inc.) of a once through continuous flow tube reactor system. Diluted (0.05×) LB medium was used as a growth medium. Biofilms were grown for 6 days under flowing conditions at 22° C.

Susceptibility Testing of $P.$ $aeruginosa$ biofilms to FAC water:

To determine the effect of FAC water treatment on biofilms, $P.$ $aeruginosa$ biofilms were grown for 6 days as described above and subsequently treated with FAC water for up to 60 min under flowing conditions (0.1 ml/minute). Upon treatment, biofilm cells were harvested from the interior surface by pinching the tube along its entire length resulting in extrusion of the cell material from the lumen. The resulting cell paste was directly collected into FAC water-neutralizing solution and homogenized for 30 sec to disrupt cell clusters. Biofilm viability was determined by the number of colony-forming units (CFU) using serial dilution plate counts. Untreated biofilms were used as controls. Experiments were done in triplicate.

Visualization of the effect of FAC water treatment on biofilms by microscopy. To visualize the effect of FAC water treatment on the viability of $P.$ $aeruginosa$ biofilm cells, biofilms were grown in a once-through, continuous culture flow cell for 6 days as described previously. The flow cell was constructed of anodized aluminum containing a chamber (4.0 mm×1.3 cm×5.0 cm) having two glass surfaces, one being a microscope slide and the other being a glass coverslip serving as the substratum. Briefly, $P.$ $aeruginosa$ cells grown to mid-exponential phase (4 ml) served as the inoculum and were injected into a septum 4 cm upstream from the flow cell. Bacteria were allowed to attach to the glass substratum for 1 h prior to initiating flow. The flow rate of the system was adjusted to 0.1 ml/min. Flow through the chamber was laminar, with a Reynolds number of <0.5, having a fluid residence time of 40 min. After 6 days of biofilm growth, biofilms were stained with Live/Dead® BacLight™ (Invitrogen, Eugene, Oreg.) and subsequently viewed by confocal scanning laser microscopy (CSLM) with a LD-Apochrome 40×/0.6 lens using a LSM 510 Meta inverted microscope (Zeiss, Heidelberg, Germany). Once images of untreated biofilms were acquired, FAC water was supplied at a flow rate of 0.1 ml/min for a period of 60 min. Images were acquired every 10-15 min to visualize the effect of FAC water on biofilm viability and biofilm architecture. To ensure proper staining of the biofilm during treatment with FAC water, Live/Dead® BacLight™ stain was continuously supplied. Quantitative analysis of epifluorescence microscopic images obtained from flow cell-grown biofilms at the 6-day time point before, during and upon completion of the treatment with FAC water was performed with COMSTAT image analysis software. Untreated biofilms were used as controls. Experiments were done in triplicate.

Induction of Biofilm Disaggregation By Treatment With FAC Waters:

To determine whether the OIS-125 or OIS-200 waters induce biofilm disaggregation, 5-day old biofilms were treated for 60 min with any of the two FAC waters under flowing conditions as described previously. The effluent was collected over time into 20 µl 50 mM sodium thiosulfate and 20 µl 0.1% sodium azide to neutralize the FAC water. A total of 200 µl was collected for each time point (2 min intervals). The absorbance of the effluent was read at 570 nm. In addition, effluent was analyzed by microscopy to determine the presence and size of cell clusters. A total of 20 microscopic fields (at 400× magnification) per effluent were analyzed. Experiments were done a total of 4 times. Saline treated biofilms were used as controls.

Example 1

This Example demonstrates that FAC waters are effective against planktonic $Pseudomonas$ $aeruginosa$ cells.

The killing efficiency of stable, pH neutral OIS-80 was comparable to those obtained with unstable, acidic FAC waters (pH 2.3-2.7). The efficacy of this solution and that of two other stable, pH neutral, FAC water with higher active oxychlorine content (i.e. OIS-125, 125 mg/L; OIS-200, ~200 mg/L) were tested against $P.$ $aeruginosa$ cells grown planktonically and as biofilms.

The efficacy of the three FAC waters against exponential phase $P.$ $aeruginosa$ was tested. To do so, a bacterial suspension (approximately $10^8$ CFU/ml) was incubated with FAC water for 20 sec., 5 min. and 20 min. at room temperature. The surviving population at each sampling time was determined on TSA. Under these conditions, an exposure time of 20 seconds was sufficient to completely inactivate $P.$ $aeruginosa$ (>99.999% reduction) with any of the three FAC waters. Thus, a log reduction of more than 5 occurred for samples treated for only 20 seconds with these FAC waters. Further, treatment of $P.$ $aeruginosa$ with bacitracin (33 U/ml) for the same amount of time (20 sec.-20 min.) was ineffective and did not result in reduction of viability (data not shown).

Example 2

This Example demonstrates that OIS-125 and OIS-200 are effective against stationary phase $P.$ $aeruginosa$ cells.

The efficacy of FAC water for stationary phase $P.$ $aeruginosa$ using penicylinders was studied. In brief, a film of bacterial cells dried on a surface of stainless steel carriers was exposed to the test substance for 10 min. Untreated carriers were used as control and for the two bacterial suspension tested, a total of $4.7\times10^6$ and $9.5\times10^4$ CFU/ carrier were detected for the stationary phase *P. aeruginosa* control carrier population. Following the exposure, the carriers were transferred to vessels containing neutralizer medium and subsequently assayed for viability. Following treatment with OIS-125 and OIS-200, no growth of *P. aeruginosa* (ATCC 15442) was detected in any of the 60 subculture tubes following a 10 minute exposure period at 20° C. In contrast, growth of *P. aeruginosa* (ATCC 15442) was detected in 2 of the 60 subculture tubes following a 10 min exposure period with OIS-80 at 20° C. indicating that OIS-80 is less effective in killing stationary phase bacteria compared to OIS-125 and OIS-200.

The finding suggests that only concentrations of oxychlorine higher than 120 mg/L in the FAC water (i.e. OIS-125 and OIS-200) are effective in killing stationary phase *P. aeruginosa* cells within 10 minutes of exposure.

Example 3

This Example demonstrates that OIS-80, OIS-125 and OIS-200 are effective against *Pseudomonas aeruginosa* biofilms.

Figure 4:
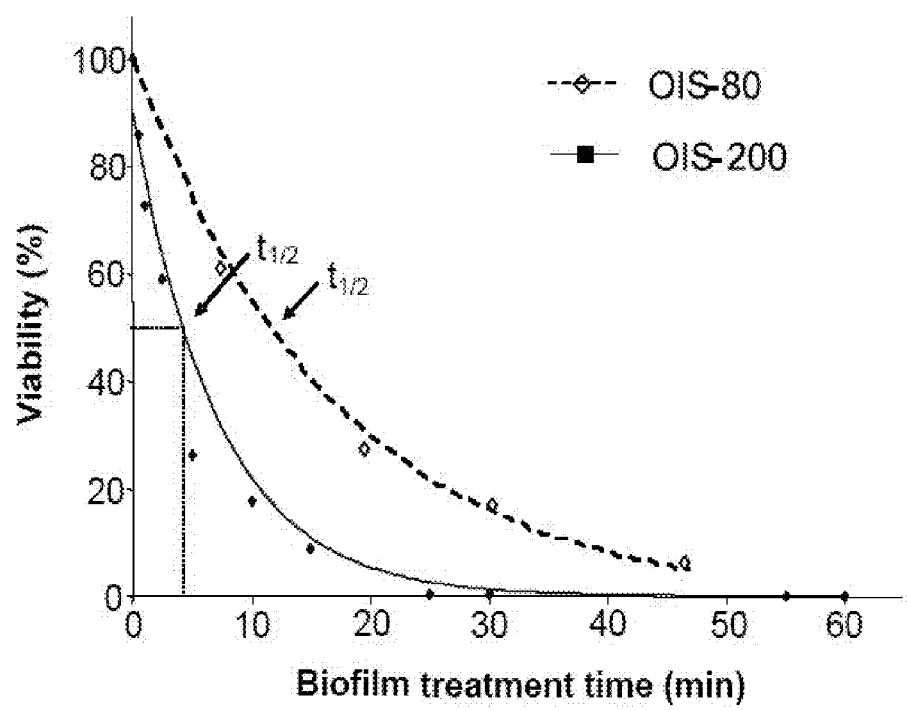
FIG. 4 depicts the determination of *P. aeruginosa* biofilm viability reduction time by the FAC water formulations OIS-80 and OIS-200.

Biofilms are considered to be highly resistant to antimicrobial agents. To determine whether FAC water is also effective in killing *P. aeruginosa* biofilms, *P. aeruginosa* was grown as biofilm in a tube reactor for six days under continuous flow. Mature biofilms were initially treated with FAC waters OIS-80 and OIS-200 having the lowest and highest concentration of chemically active oxychlorine species 80 and 200 mg/L) for 0.5-60 min. under flowing conditions to determine the time required to reduce the viability of biofilms by 50%. As shown in FIG. 4, treatment with OIS-80 or OIS-200 resulted in a 50% reduction in viability of *P. aeruginosa* biofilm cells within 10 min and 2.5 min, respectively.

Figure 5A:
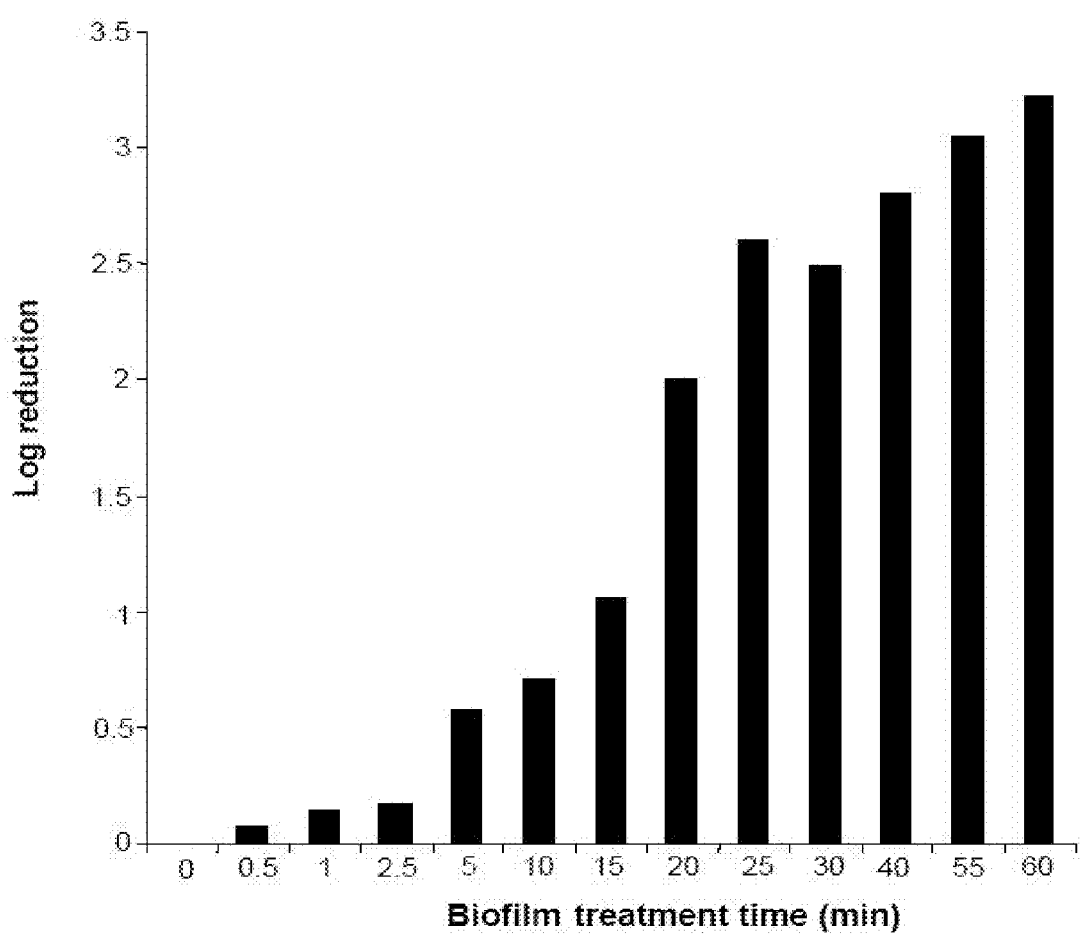
FIG. 5 depicts the effect of OIS-200 on viability of *P. aeruginosa* biofilms. (A) Viability was assessed by serial dilution to determine the total CFU/biofilm over the course of OIS-200 treatment of *P. aeruginosa* biofilms. (B) Drop plates visualizing viability of untreated biofilms (dilutions from left to right: 10-4-10-8).
Figure 5B:
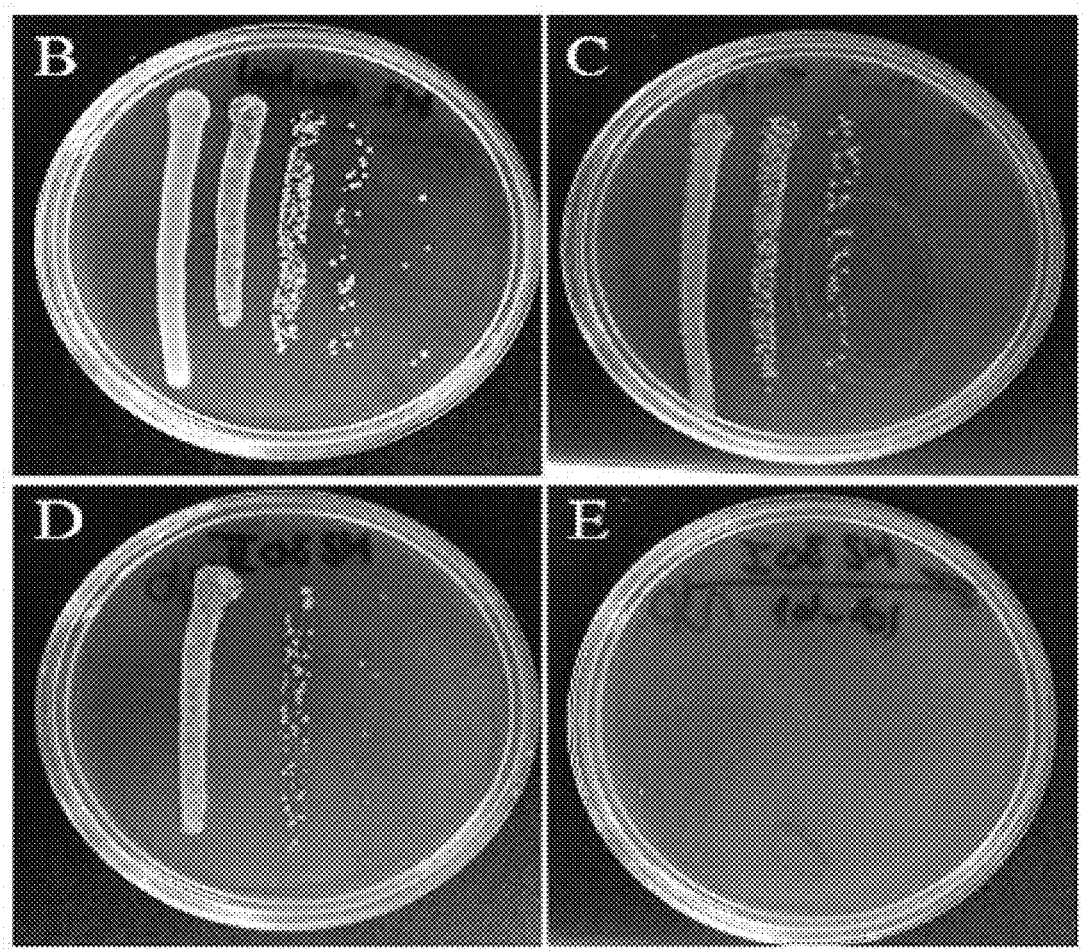
Figure 6:
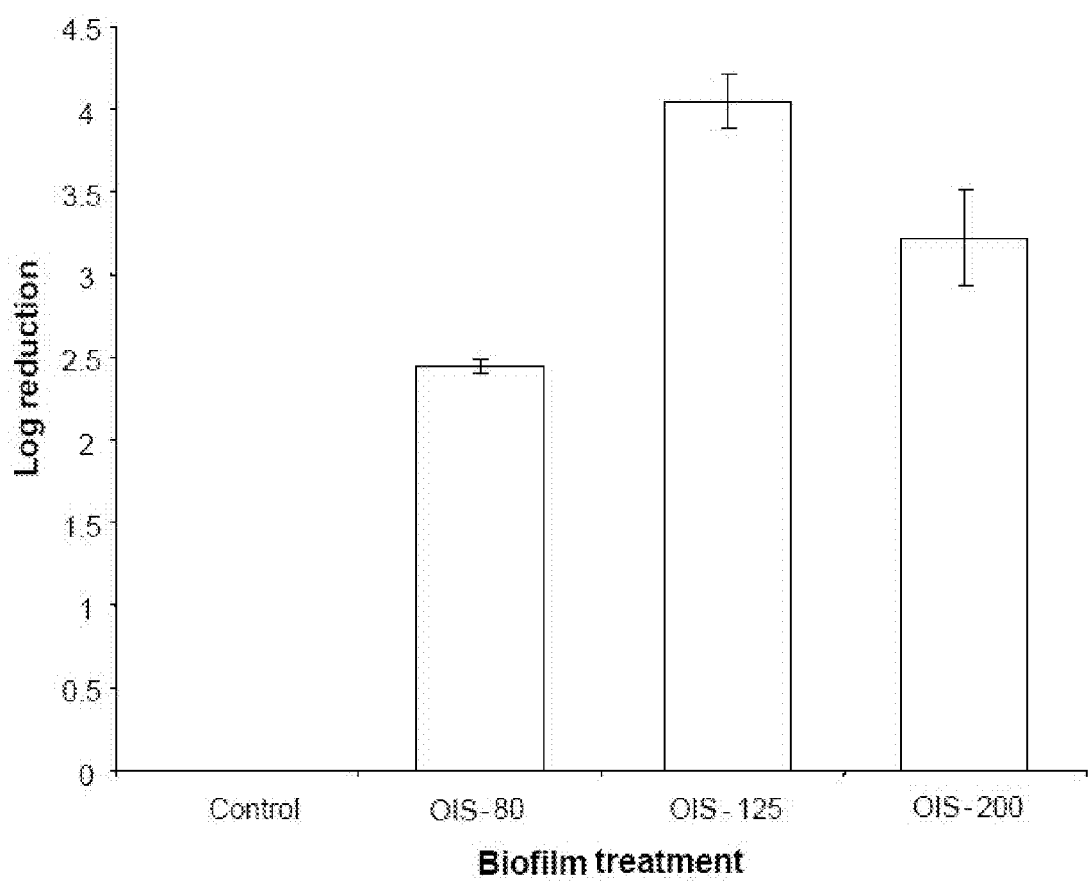
FIG. 6 depicts the efficacy of an FAC water on *P. aeruginosa* biofilm viability.
Figure 7:
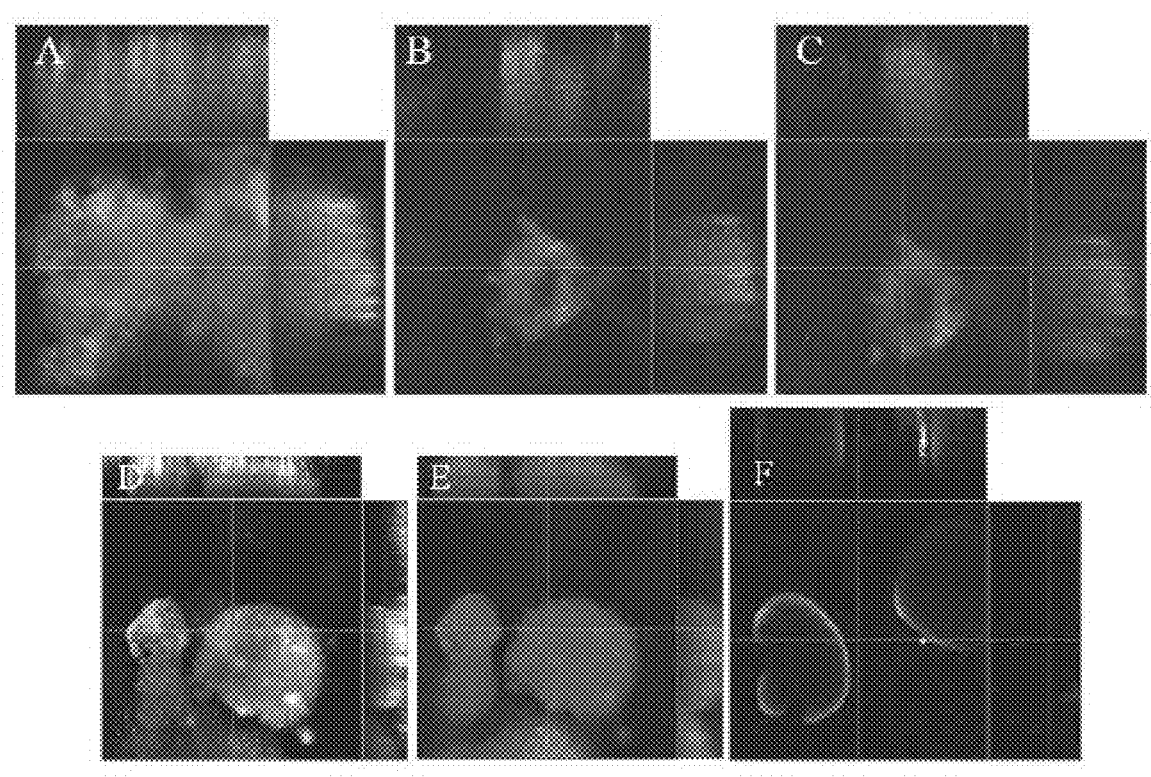
FIG. 7 depicts the microscopic characterization of the effect of OIS-200 (A-C) and OIS-125 (D-F) on *P. aeruginosa* biofilms. Confocal scanning laser microscopy images of biofilms, at a magnification of 400×, of the *P. aeruginosa* were acquired after 6 days of growth, showing the xy and xz planes. The biofilm was stained with a vital stain. The microscopic images in A-C show the same *P. aeruginosa* biofilm before (A) treatment with OIS-200 and after 10 minutes (B) and 30 minutes (C) of exposure to OIS-200. *P. aeruginosa* biofilm before (D) and after treatment with OIS-125 for 30 min (E-F). Control biofilms before (G) and after treatment (H) with saline for 30 min.

Next, the efficacy of FAC waters against *P. aeruginosa* biofilms was determined. A time course of the efficacy of OIS-200 is shown in FIGS. 5A,B. Treatment of *P. aeruginosa* biofilms with OIS-200 resulted in a 0.5 log reduction of biofilm viable cells from $2.8 \times 10^{10}$ to $7 \times 10^9$ CFU/biofilm within 5 minutes and to $9 \times 10^7$ CFU/biofilm within 30 min. of exposure (~2.5 log reduction). Continued exposure of *P. aeruginosa* biofilms to OIS-200 for 60 min resulted in a 3.3-log reduction (FIGS. 5-6). As shown in FIG. 7, FAC water having lower concentrations of the chemically active oxychlorine compound were also effective against *P. aeruginosa* biofilms. However, treatment of biofilms for 60 minutes with OIS-80 resulted in a 2.5 log reduction while treatment with OIS-125 (125 mg/L) resulted in a 4.1 log reduction (FIGS. 5 and 7). Overall, treatment with both OIS-125 and OIS-200 resulted in significantly higher log reduction of biofilm cells (P<0.01) compared to treatment with OIS-80 (FIGS. 5 and 7). No significant difference in log reduction was observed when the efficacy of OIS-125 and OIS-200 against *P. aeruginosa* biofilms was compared (P=0.67).

Example 4

This Example demonstrates the visualization of *P. aeruginosa* biofilms during treatment with FAC water.

To visualize the effect of FAC water on the *P. aeruginosa* biofilm architecture, *P. aeruginosa* biofilms grown in flow cells for 6 days, were stained using the Live/Dead stain and the biofilm architecture before and during treatment with FAC water analyzed by confocal scanning laser microscopy (CSLM). shows the three-dimensional architecture of *P. aeruginosa* biofilms before treatment with OIS-200. The majority of biofilm cells were alive (as indicated by cells stained in green) with only a few dead cells stained in red scattered throughout the biofilm. In contrast, treatment with OIS-200 for 10 min resulted in reduced viability of biofilm cells as indicated by the majority of cells throughout the biofilm being stained in red. In addition, OIS-200 affected the overall three-dimensional architecture, evident by the decrease in the overall biomass attached to the surface. Continued treatment with OIS-200 resulted in an increase in non-viable cells and a further decrease in biomass.

Reduction of the overall biomass was also observed during treatment of *P. aeruginosa* biofilms with OIS-125. Similar to OIS-200, treatment with OIS-125 for 60 min resulted in reduced viability of biofilm cells as indicated by the majority of cells stained in red (FIGS. 7D-E). In addition, evidence of biofilm disaggregation as indicated by hollowed-out microcolonies was detected (FIG. 7F). Compared to OIS-125 and OIS-200, exposure of *P. aeruginosa* biofilms to OIS-80 was less effective as indicated by a lower reduction in biofilm viability and biomass (data not shown). In contrast, no reduction in viability was observed upon treatment with saline for 30 min (FIGS. 7G-H).

Example 5

This Example demonstrates that FAC waters induce disaggregation of *Pseudomonas aeruginosa* biofilms.

Exposure to OIS-200 and OIS-125 affected the overall three-dimensional architecture, evident by the decrease in the overall biomass attached to the surface. In some cases, treatment with any of these FAC waters even resulted in biofilms dislodging from the glass surface within 10 min. To further determine the extent to which FAC water treatment resulted in the reduction of the biofilm biomass, a quantitative analysis of biofilm architecture using COMSTAT was carried out.

Over the course of 60 min treatment with OIS-200, the average biomass decreased 12-fold, from about 45 $\mu m^3/\mu m^2$ to less than 4 $\mu m^3/\mu m^2$. Furthermore, average thickness of the biofilm and roughness (a measure of biofilm heterogeneity, Table 1) was affected. The average thickness decreased 9-fold from ~67 µm to approximately 8 µm (Table 1). Similarly, treatment with OIS-125 resulted in a >7-fold reduction in the biofilm biomass which decreased from about 37 $\mu m^3/\mu m^2$ to less than 5 $\mu m^3/\mu m^2$, and a 7-fold decrease in average thickness. The roughness coefficient increased from 0.7 to 1.6 (Table 1). The least reduction in biofilm biomass and biofilm thickness was detected for OIS-80. Treatment with OIS-0180 only resulted in ~2-fold reduction in both biofilm biomass and thickness (Table 1).

TABLE 1

COMSTAT analysis. Quantitative analysis of biofilm structure of
P. aeruginosa before and after 60 min of treatment with FAC water[b].

| Treatment | Biomass ($\mu m^3/\mu m^2$) | Average thickness ($\mu m$) | Roughness | Fold reduction in biomass | Fold reduction in average thickness |
|---|---|---|---|---|---|
| Before treatment | | | | | |
| Control (saline) | 33.2 (6.3) | 38.72 (11.5) | 0.6 (0.11) | | |
| OIS-80 | 36.41 (2.6) | 56.0 (16.9) | 0.87 (0.313) | | |
| OIS-125 | 37.06 (8.2) | 59.2 (10.1) | 0.68 (0.29) | | |
| OIS-200 | 44.72 (3.2) | 69.67 (2.52) | 0.42 (0.14) | | |
| After 60 min of treatment | | | | | |
| Control (saline) | 33.04 (7.3) | 39.2 (10.3) | 0.6 (0.05) | 1.0 | 0.98 |
| OIS-80 | 21.92 (2.1) | 23.13 (6.2) | 0.77 (0.2) | 1.7 | 2.4 |
| OIS-125 | 5.17 (4.4) | 6.65 (7.24) | 1.59 (0.32) | 7.2 | 8.9 |
| OIS-200 | 3.53 (2.9) | 8.26 (4.3) | 1.27 (0.49) | 12.7 | 8.1 |

[a]Values are means of data from six z-series image stacks.
[b]The results of a representative assay are presented.

Example 6

This Example demonstrates that OIS-125 induces biofilm disaggregation as effectively as treatment with OIS-200.

Figure 8:
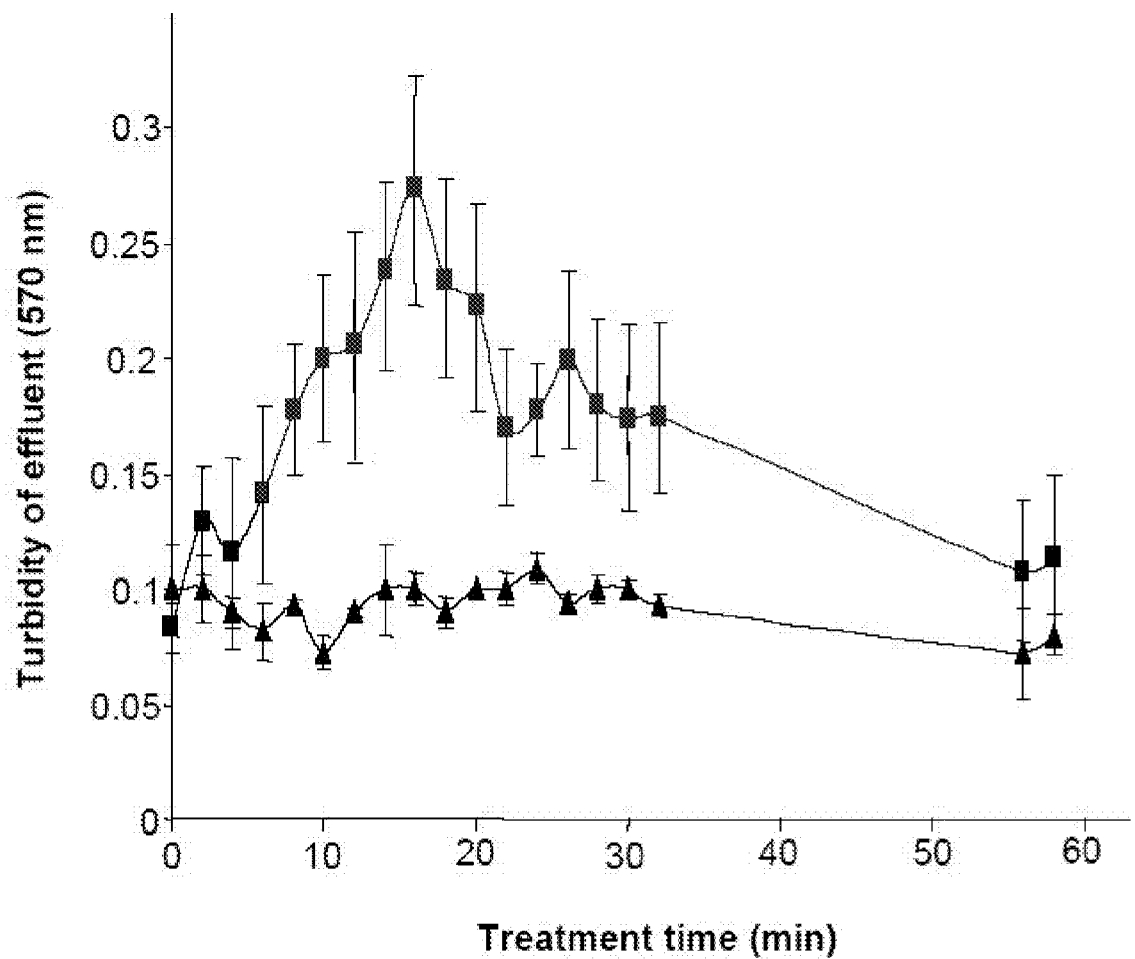
FIG. 8 demonstrates that OIS-125 induces biofilm disaggregation. Biofilm disaggregation was evaluated over a period of 60 min upon treatment with saline (▲, control) or OIS-125 (■). Error bars indicate standard deviation.

The visual and quantitative evaluation of the FAC water treatment effect on biofilm architecture suggested that the efficacy of FAC water against biofilms may be based on both killing of biofilm cells and disaggregating cells from the biofilm. Further, whether FAC water treatment resulted in biofilm disaggregation was investigated. Biofilm disaggregation was examined by monitoring the biofilm effluent as previously described. The effluent was collected over a period of 60 min. and the turbidity determined at 570 nm. One example of a typical result obtained using OIS-200 is shown in FIG. 8. Compared to biofilms treated with saline, OIS-200 induced disaggregation of biofilms as indicated by the increase in absorbance in the effluent during treatment (FIG. 8). Similar results were obtained for OIS-125 (data not shown).

To further determine whether FAC water treatment resulted in disaggregation of biofilm cells as individual planktonic cells or in sloughing of biofilms (removal of cell clusters), the effluent of biofilms treated with saline, OIS-125 and OIS-200 was analyzed by microscopy. The visual inspection of biofilm effluents revealed the presence of both, planktonic cells and cell clusters/aggregates independent of treatment of biofilms. Accordingly, it was further investigated whether FAC water treatment resulted in increased disaggregation of cell clusters or aggregates compared to saline treatment. An "aggregate" composed of more than 3 bacterial cells was considered to be a cell cluster. The total number of clusters present in 20 different microscopic fields of view per effluent as well as the dimension of each cell cluster was noted. As shown in Table 2, the average number of cell cluster in the effluent of OIS-125-treated biofilms was 1.13 having an average cluster diameter of 33.3 µm. Treatment with OIS-200 resulted in an average of 0.35 cell clusters per field view having an average diameter of 24.7 µm. Similarly, an average of 0.33 cell clusters with an average diameter of 20.4 µm were detected in effluents of biofilms exposed to saline (Table 2). Overall, exposure of biofilms to FAC waters did not result in a significant increase in the number of cell clusters or increased cell cluster diameter in the effluent when compared to saline treated biofilms (P>0.3).

Example 7

Materials and Methods

One animal was used for this study. Swine are used as our experimental research animal since their skin is morphologically and biochemically similar to human skin. The young female specific pathogen free (SPF: Looper Farms, North Carolina) pig, weighing 25-30 kg, on arrival, was kept in house for approximately a week before initiating the experiment. The animal was fed a basal diet ad libitum and housed individually controlled temperature (19-21° C.) and light/dark cycles (12 h/12 h LD).

The flank and back of experimental pig was clipped with standard animal clippers on the day of the experiment. The skin was prepared for wounding by washing with a non-antibiotic soap (Neutrogena Soap Bar; Johnson and Johnson, Los Angeles, Calif.) and sterile water. Each animal was anesthetized intramuscularly with tiletamine HCl plus zolazepam (5 mg/kg) (Telazol; Laderle Parenterals Inc, Carolina, Puerto Rico), xylazine (0.2 mg/kg) (X-jet; *Phoenix* Scientific Inc, St. Joseph, Mo.), and atropine (0.05 mg/kg) (Atrojet SA; *Phoenix* Scientific Inc, St. Joseph, Mo.) followed by mask inhalation of an isoflurane (Isothesia; Abbott Laboratories, Chicago, Ill.) and oxygen combination.

Sixty (60) second-degree burn wounds were made in the paravertebral and thoracic area by using five specially designed cylindrical brass rods weighing 358 g each that were heated in a boiling water bath to 100° C. A rod was removed from the water bath and wiped dry before it is applied to the skin surface to prevent water droplets from creating a steam burn on the skin. The brass rod was held at a vertical position on the skin (six seconds), with all pressure supplied by gravity, to make a burn wound 8.5 mm diameter×0.8 mm deep. Immediately after burning, the roof of the burn blister was removed with a sterile spatula. Fifteen (15) burn wounds were assigned to one of four recovery groups. All burn wounds were inoculated with a pathogenic strain of *Pseudomonas aeruginosa* (see below) and all wounds were covered with Tegaderm dressings. The dressings were secured in place by wrapping the animals with self-adherent bandages (Petflex; Andover, Salisbury, Mass.). Wounds were covered for 1 hour prior to initial treatment to allow bacteria enough time to colonize the wound.

A fresh culture of pathogenic isolate obtained Karin Sauer (SUNY Binghamton, N.Y.), was used in these studies (*Pseudomonas aeruginosa* PAO1). The freeze-dried bacteria culture was recovered from 15% glycerol stocks (−80° C.). All inoculum suspensions were made by scraping the overnight growth from a culture plate into 5 ml of normal saline. This resulted in a suspension concentration of approximately $10^8$ colony forming units/ml (CFU/ml). The suspension was diluted to make an inoculum suspension with a concentration of $10^6$ CFU/ml. A small amount of the inoculum suspension was plated onto culture media to quantify the exact concentration of viable organisms prior to the experiment. The inoculum suspension was used directly to inoculate each site. A 25 µl aliquot of the suspension was deposited into a sterile glass cylinder (22 mm diameter) in the center of each wound site. The suspension was lightly scrubbed into the test site for ten seconds using a sterile teflon spatula. All wounds were covered with a Tegaderm dressing (per sponsor request).

One hour after wounding and inoculation, the wounds were treated with 5 mL of treatment as described below. All wounds were treated by individually encompassing the wounds with a 22 mm sterile steel cylinder and irrigating twice with 2.5 ml of treatment for 1 minute. The treatment was then aspirated out, the cylinder removed and any excess fluid outside the cylinder area wiped up with sterile gauze without disturbing the wound. Following final irrigation, wounds were individually covered with polyurethane (Tegaderm) dressing. All wounds received a final treatment immediately prior to bacterial recovery.

Wounds from each treatment group were divided in four subgroups. The subgroups were treated once or twice daily and recovered on day 3 or day 7. Weekend treatments were done once daily for all groups and subgroups.

All scrub recoveries were made using all purpose neutralizing scrub solution. Wounds were cultured only once by encompassing each one with a sterile cylinder (22 mm outside diameter). The wounds were recovered for biofilm bacteria by using one mL of scrub solution which was pipetted into the cylinder covering the wound. The wound was then scrubbed for 30 seconds with a sterile Teflon spatula to remove the firmly attached bacteria.

Once the specimens were collected, serial dilutions (10-fold) were made and the number of *P. aeruginosa* organisms was quantified using the Spiral Plater system. The selective media for *P. aeruginosa* was *Pseudomonas* Agar Base with CN Supplement. After plating, all samples were incubated aerobically overnight at 37° C. After the incubation period colonies on the plates were counted and the colony forming units per ml (CFU/ml) and Log CFU/ml, calculated.

Results and Data Analysis

At 1 hour, 3 days and 7 days post-inoculation, the challenge pathogen was recovered from the sites and the mean Log CFU/ml and standard deviation determined at each time and for each treatment.

Bacterial counts of *Pseudomonas aeruginosa* at each assessment time point. On day 3, the twice daily treatments with OIS1080, OIS1150, OIS1220 and saline reduced 0.5 Log CFU/ml the number of *P. aeruginosa* recovered as compared to once daily. Treatment OIS1150 was found to be the treatment with the lowest Log CFU/ml, (7.43±0.37 and 6.99±0.49) with both treatment regimens. All treatment groups had increased bacterial counts compared to the 1 hour recovery.

On day 7, twice daily treatment with OIS1080, OIS1150, OIS1220 and saline reduced the number of *P. aeruginosa* recovered as compared to once daily treatment. The treatment OIS1150 twice daily regimen was found to be the treatment with the lowest Log CFU/ml reduction (0.59±0.43) as compared with once daily regimen. All treatment groups had increase bacterial counts compared to 1 hour post inoculation recovery.

Recovery at day 7 for the daily treatment group with OIS1080, OIS1150, OIS1220 and saline resulted in reduced number of *P. aeruginosa* recovered as compared to the day 3 recoveries. Treatments OIS1080 and OIS1150 were found to be the treatments with the lowest Log CFU/ml at both assessment times. On day 7 the number of bacteria recovered from saline treatment was similar compared with treatment OIS1220. All treatment groups had increase bacterial counts compared to the 1 hour recovery.

Recovery of the twice daily treatment groups with OIS1080, OIS1150, OIS1220 and saline on day 7 resulted in reduced numbers of *P. aeruginosa* recovered as compared to twice daily treatment on day 3. Treatment OIS1150 was found to be the treatment with the lowest Log CFU/ml at both assessment times. All treatment groups had increase bacterial counts compared to the 1 hour recovery.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or reducing the incidence of inflammation associated with a biofilm containing an infectious microorganism on an oral mucosal tissue in the oral cavity of a mammal, the method comprising disaggregating the biofilm by contacting the biofilm on the oral mucosal tissue with a therapeutically effective amount of free available chlorine (FAC) water for at least about 30 minutes, wherein:
(a) the pH of the FAC water is from about 7.3 to about 7.5,
(b) the concentration of oxychlorine species in the FAC water is 150 mg/L to 200 mg/L, and
(c) the infectious microorganism is selected from *Pseudomonas* sp., *Haemophilus* sp., *Pneumococcus* sp., *Mycobacterium* sp., *Stenotrophomonas* sp., *Streptococcus* sp., *Escherichia* sp., *Mycoplasma* sp., and combinations thereof,
to treat or reduce the incidence of the inflammation associated with the biofilm.

2. The method of claim 1, wherein the infectious microorganism is in a preinfectious commensal state.

3. The method of claim 1, wherein the mammal is a human patient.

4. The method of claim 3, wherein the mammal has an immunodeficiency.

5. The method of claim 3, wherein the FAC water is administered as a lavage, drop, rinse, spray, mist, aerosol, steam or combination thereof.

6. The method of claim 3, wherein the FAC water is administered in the form of droplets having a diameter in the range of from about 0.1 micron to about 100 microns.

7. The method of claim 3, further comprising administering at least one antibiotic agent.

8. The method of claim 1, wherein the FAC water is stable for at least about two months.

9. The method of claim 1, wherein the FAC water comprises a mixture of cathode water and anode water.

10. The method of claim 1, wherein the oxychlorine species is selected from the group consisting of hypochlorous acid, hypochlorite ions, sodium hypochlorite, and mixtures thereof.

11. The method of claim 1, wherein the FAC water reduces the concentration of viable bacteria in the biofilm by at least about 2 logs within 60 minutes.

12. A method of treating or reducing the incidence of inflammation associated with a biofilm containing an infectious microorganism on an oral mucosal tissue in the oral cavity of a mammal, the method comprising disaggregating the biofilm by contacting the biofilm with a therapeutically effective amount of free available chlorine (FAC) water for at least about 30 minutes, wherein:
(a) the pH of the FAC water is from about 7.3 to about 7.5,
(b) the concentration of oxychlorine species in the FAC water is 150 mg/L to 200 mg/L, and
(c) the infectious microorganism is selected from *Pseudomonas* sp., *Haemophilus* sp., *Pneumococcus* sp., *Mycobacterium* sp., *Stenotrophomonas* sp., *Streptococcus* sp., *Escherichia* sp., *Mycoplasma* sp., and combinations thereof,
to treat or reduce the incidence of the inflammation associated with the biofilm, and
wherein the method further comprises administering to the mammal at least one antibiotic agent.

13. The method of claim 12, wherein the infectious microorganism is in a preinfectious commensal state.

14. The method of claim 12, wherein the mammal is a human patient.

15. The method of claim 12, wherein the FAC water is stable for at least about two months.

16. The method of claim 12, wherein the FAC water comprises a mixture of cathode water and anode water.

17. The method of claim 12, wherein the oxychlorine species is selected from the group consisting of hypochlorous acid, hypochlorite ions, sodium hypochlorite, and mixtures thereof.

18. The method of claim 1, comprising contacting the biofilm with the FAC water for at least about 60 minutes.

* * * * *